United States Patent [19]

Takei et al.

[11] Patent Number: 4,603,124

[45] Date of Patent: Jul. 29, 1986

[54] SURFACTANT AND PHARMACEUTICAL COMPOSITIONS CONTAINING SAME

[75] Inventors: Tsunetomo Takei, Kuki; Yosaku Kanazawa, Nakano; Kazuo Masuda, Yokosuka; Yuji Tanaka, Toda, all of Japan

[73] Assignee: Tokyo Tanabe Company, Limited, Japan

[21] Appl. No.: 583,866

[22] Filed: Feb. 27, 1984

[30] Foreign Application Priority Data

Oct. 3, 1983 [JP] Japan .................. 58-38189

[51] Int. Cl.$^4$ ...................... A61K 31/685; C07F 9/02
[52] U.S. Cl. ......................... 514/78; 514/2; 514/975; 260/403
[58] Field of Search ........... 424/199; 260/403; 514/2, 78, 975

[56] References Cited

U.S. PATENT DOCUMENTS

| 4,312,860 | 1/1982 | Clements | 424/199 |
| 4,338,301 | 7/1982 | Tetsuro et al. | 424/95 |

OTHER PUBLICATIONS

Suzuki, Journ. Lipid Research, vol. 23, pp. 62–69 (1982) (Corresponding to Chem. Abstract 96:99813j (1982)).
Suzuki et al., Exp'l Studies on the Pulmonary Surfactant, Reconstitution of Surface-Active Material, Chem. Abstracts 96:99812h (1982).
Kokubo et al., Trial Preparations of Artificial Surfactant, Effect on Lung Lavaged Rabbits, Chem. Abstracts 99:82279d (1983).
Suzuki et al., Investigation on the Surface Activity of Lipid–Protein Complexes Reconstituted from Phospholipids and Surfactant Apoprotein, Chem. Abs. 99:66246k (1983).
King et al., Surface Active Materials from Dog Lung, II, (Composition . . . , Chem. Abstracts 77:162283m (1972a).
King et al., Surface-Active Materials from Dog Lung, I, Method of Isolation, Chem. Abstracts 77:123604x (1972b).
Henderson et al., . . . Pulmonary Surfactant Lipid Removed from the Lung of Beagle Dogs by Lavage, Chem. Abstracts 81:148063r (1974).
Guerrero et al., Interference of Free Fatty Acids on Pulmonary Surfactant in the Rabbit, Chem. Abstracts 97:214807v (1982).

*Primary Examiner*—Ethel G. Love
*Attorney, Agent, or Firm*—McGlew and Tuttle

[57] ABSTRACT

A surfactant having the capacity of reducing the surface tension in pulmonary alveoli significantly is provided. The surfactant consists essentially of, based on the total weight of the surfactant, 50.6–85.0% of a chlorine phosphogylceride, 4.5–37.6% of an acid phospholipid, 4.6–24.6% of a fatty acid or its analogue and 0.1–10.0% of a lipoprotein derived from the lung of a mammal. These components cooperate to form a kind of film at a gas-liquid interface within pulmonary alveoli and reduce the surface tension. A pharmaceutical composition comprising the surfactant is useable for the clinical treatment of respiratory distress syndrome.

26 Claims, 5 Drawing Figures

SURFACTANT AND PHARMACEUTICAL COMPOSITIONS CONTAINING SAME

FIELD AND BACKGROUND OF THE INVENTION

Deficiency of the so-called pulmonary surfactant (i.e., the material that reduces intra-alveolar surface tension) causes a failure of expansion of the lungs which leads to the impairment of pulmonary ventilation essential for the maintenance of life. Disorders exhibiting such a symptom are generically named "respiratory distress syndrome (hereinafter referred to briefly as RDS)". It is known that this disease frequently occurs not only in premature infants but also in adult patients with bacterial infection, gas intoxication or traumata.

In recent years, great importance has been attached to the use of a substitute for the deficient pulmonary surfactant in the treatment of RDS. A large number of previous studies on the pulmonary surfactant have established certain physicochemical criteria for such a substitute. In a brief summary, the main criteria are as follows: (1) the substitute must be capable of reducing the surface tension of physiological saline to 10 dynes/cm or less (the most important criterion); (2) the substitute must be able to become adsorbed to and spread over a gas-liquid interface rapidly; and (3) the substitute must give a good surface tension-surface area hysteresis curve (hereinafter referred to briefly as a hysteresis curve) [American Journal of Physiology, 223(3), 715, 1972; Biochimica et Biophysica Acta, 344, 241, 1974; The New England Journal of Medicine, 280, 1298, 1969].

A number of well-known materials have been reported to be useable as substitutes for the pulmonary surfactant. They include, for example, mixtures of phosphatidylcholine and phosphatidylglycerol (hereinafter referred to briefly as PC-PG mixtures; Pediatric Research, 11, 573, 1979), compositions consisting essentially of dipalmitoylphosphatidylcholine and fatty alcohols (hereinafter referred to briefly as DPPC compositions; Japanese Patent Laid-Open No. 99524/1982), and a material comprising, in specific proportions, phospholipid, neutral fat, total cholesterol, carbohydrate and protein which are all obtained from the lung tissue of mammals (hereinafter referred to briefly as TA-546; Japanese Patent Laid-Open No. 160721/'80). However, confirmatory studies carried out by the present inventors have revealed that the PC-PG mixtures are incapable of reducing the surface tension of physiological saline to 10 dynes/cm or less and that the DPPC compositions are slow in becoming adsorbed to and spreading over a gas-liquid interface and do not give a good hysteresis curve. Thus, these materials have chemical compositions consisting essentially of or containing the main components of the pulmonary surfactant but, nevertheless, do not fulfill the above-described criteria. On the other hand, TA-546 conforms to the above-described criteria. However, since its chemical composition is complicated, it is expected that TA-546 may contain undesired components exerting an influence on its pulmonary surface activity.

Specifically, per Table 1 of Tetsuro et al, U.S. Pat. No. 4,338,301, issued July 6, 1982, of overlapping inventorship herewith (and which corresponds to said Japanese Patent Laid-Open No. 160721/'80), it is clear that in addition to (1) 75.6 to 95.5% phospholipid, constituting its principal component (and which is itself composed of 63.0 to 85.5% phosphatidylcholine, 3.0 to 12.0% phosphatidylglycerol, 2.5 to 7.7% phosphatidylethanolamine, 5.7 to 7.0% sphingomyelin, 2.4 to 7.4% phosphatidylinositol and phosphatidylserine collectively, 0.5 to 2.1% lysophosphatidylcholine, and not greater than 1.0% others, TA-546 contains four other components: (2) 1.8 to 14.0% neutral lipid or neutral fat (whose content is calculated in glycerol trioleate equivalent and therefore is composed mostly of triglycerides, (3) 0.0 to 3.0% total cholesterol, (4) 0.1 to 1.5% carbohydrate, and (5) 0.5 to 5.0% protein, plus (6) 1.7 to 6.0% water, wherein the ratio of the (1) phospholipid content to the (5) protein content is 15.0 or greater, and the content of phosphatidylcholine having two saturated fatty acid residues based on the total phosphatidylcholine in the (1) phospholipid is 67.5 to 90.3%.

Hence, as to the (1) phospholipid fraction, TA-546 contains not only 63.0 to 85.5% phosphatidylcholine, but also many minor components including acid phospholipids such as phosphatidylglycerol, phosphatidylinositol and phosphatidylserine, and other phospholipids such as phosphatidylethanolamine, sphingomyelin, lysophosphatidylcholine, etc. Accordingly, it is reasonably to be expected that undesired components having no favorable effect or, more important, instead having adverse effects on the pulmonary surface activity of TA-546 may be present not only among the aforesaid four components (aside from water) but also among the minor components of the (1) phospholipid fraction.

SUMMARY OF THE INVENTION

As a result of close investigation on the individual components constituting the pulmonary surfactant and TA-546, the present inventors have found that the components truly essential for the development of pulmonary surface activity are four substances, i.e., a choline phosphoglyceride (such as dipalmitoylphosphatidylcholine or the like), an acid phospholipid (such as phosphatidylglycerol, phosphatidylserine or the like), a fatty acid (such as palmitic acid or the like) or its analogue, and a lipoprotein derived from the lung of a mammal and that, when these components are present in specific proportions, they co-operate to form a kind of film at a gas-liquid interface within pulmonary alveoli and thereby reduce the surface tension. The present invention has been completed on the basis of these findings.

In one aspect of the present invention, there is provided a surfactant consisting essentially of a choline phosphoglyceride, an acid phospholipid, a fatty acid or its analogue, and a lipoprotein derived from the lung of a mammal, characterized in that the choline phosphoglyceride content is 50.6 to 85.0%(w/w), the acid phospholipid content is 4.5 to 37.6%(w/w), the fatty acid or its analogue content is 4.6 to 24.6%(w/w), and the lipoprotein content is 0.1 to 10.0%(w/w), all based on the total weight of the surfactant. In another aspect of the present invention, there are provided pharmaceutical compositions useable for the treatment of respiratory distress syndrome containing the above-described surfactant as active ingredient. In still another aspect of the present invention, there are provided methods for treating respiratory distress syndrome comprising administering the above-described pharmaceutical compositions.

For an understanding of the principles of the invention, reference is made to the following description of typical embodiments thereof as illustrated in the accompanying drawings.

DESCRIPTION OF THE PREFERRED EMBODIMENTS

Figure 1:
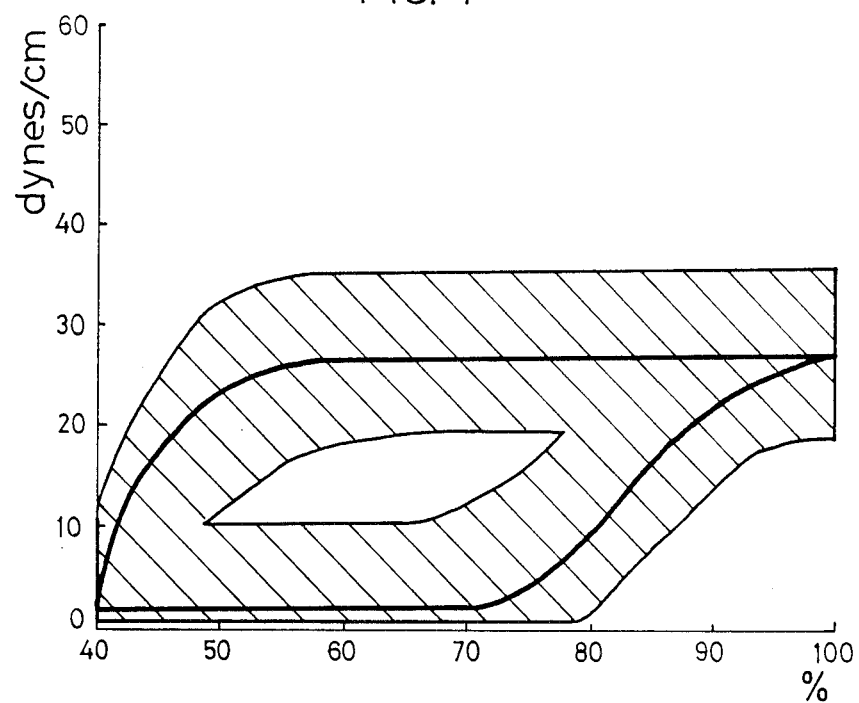
FIGS. 1 to 3 are diagrammatic illustrations of hysteresis curves showing the surface tension of physiological saline against the surface area thereof.
Figure 2:
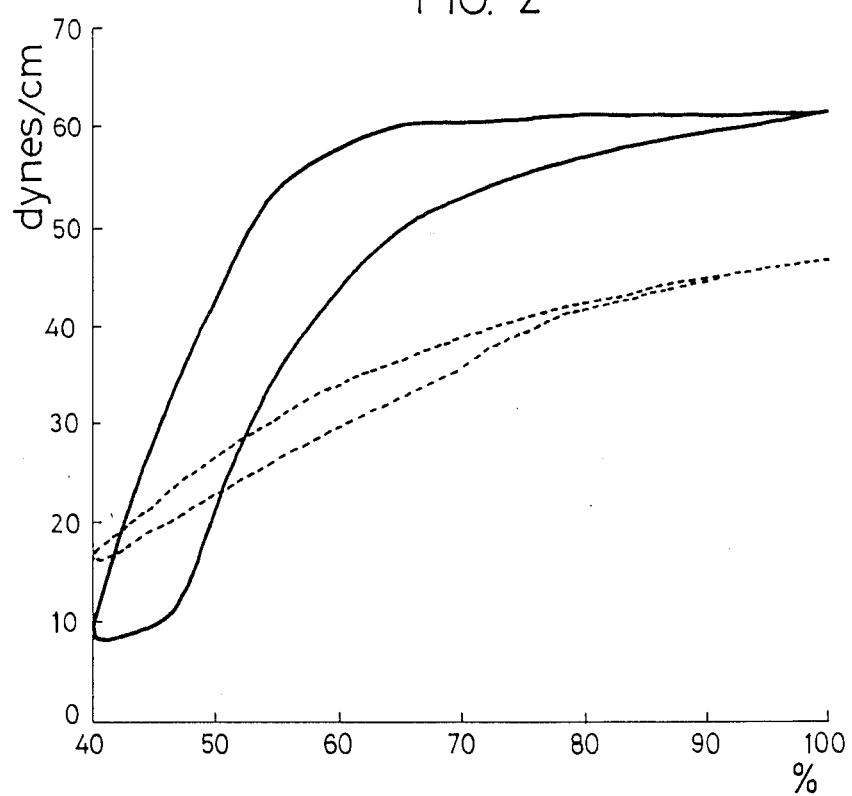
Figure 3:
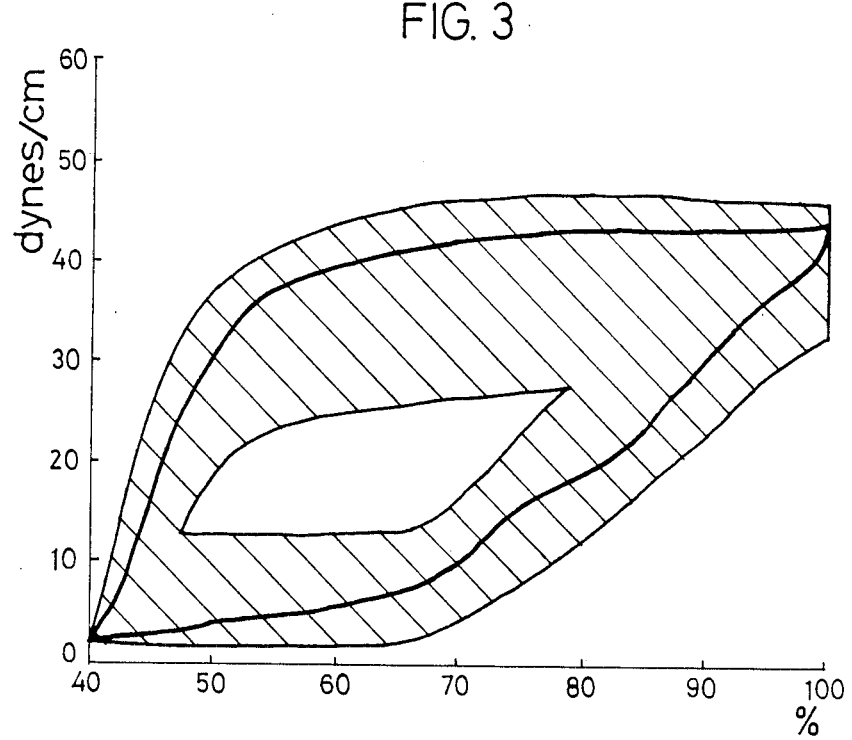

FIGS. 1 to 3 diagrammatically illustrate hysteresis curves recorded by measuring the surface tension of physiological saline with an Acoma Wilhelmy surface tension balance (Acoma Igaku Kogyo Co., Ltd.) and plotting the measured data with an X-Y recorder (model RW-11; Rika Denki Kogyo Co., Ltd.). In FIGS. 1 and 3, measurements were made at 37° C. after the surfactant of the invention and TA-546, respectively, were added dropwise to the surface of physiological saline in an amount of 1.0 to 2.0 µg per square centimeter of the surface area. In these figures, the shaded portion indicates the region into which the recorded hysteresis curves fall, and the bold solid line in said region represents an exemplary hysteresis curve. FIG. 2 diagrammatically illustrates hysteresis curves recorded in the same manner by using a typical PC-PG mixture and a typical DPPC composition, respectively. In this figure, the solid line represents the hysteresis curve of the DPPC composition and the dotted line represents the hysteresis curve of the PC-PG mixture. In each figure, the surface tension is plotted as ordinate and the surface area expressed in percentage of the maximum surface area (54.0 cm$^2$) as abscissa.

Figure 4:
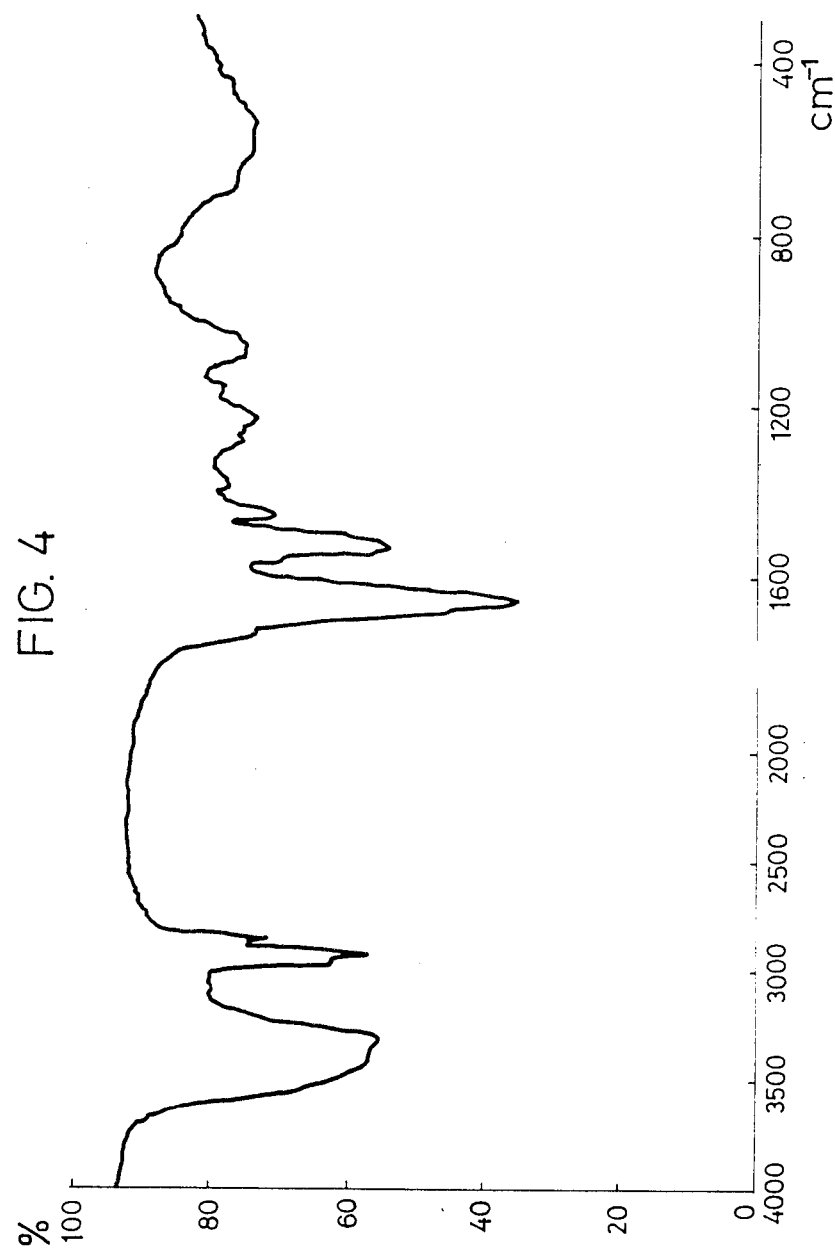
FIG. 4 is an infrared absorption spectrum of the lipoprotein present in the surfactant of the invention.

FIG. 4 is an infrared absorption spectrum, as measured in a KBr tablet, of the lipoprotein constituting one major component of the surfactant of the invention.

Figure 5:
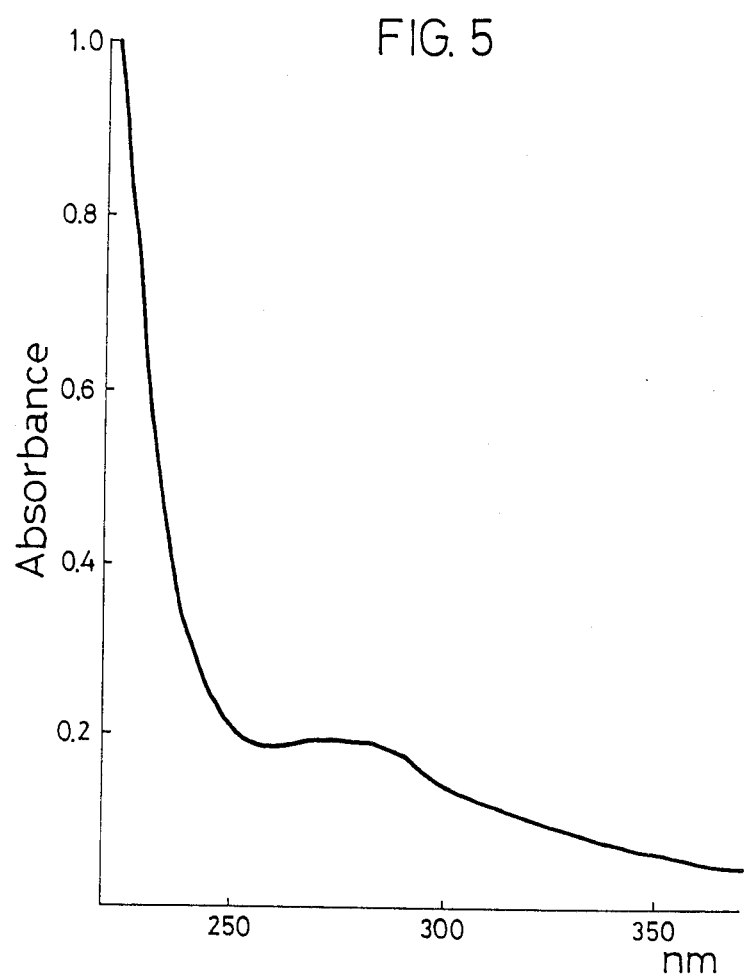
FIG. 5 is an ultraviolet absorption spectrum of the same lipoprotein.

FIG. 5 is an ultraviolet absorption spectrum of the same lipoprotein as measured by a solution of 1.37 mg of the lipoprotein in 10 ml of a 1% aqueous solution of sodium dodecyl sulfate.

It is thought that, in the surfactant of the invention, the choline phosphoglyceride is the major component constituting the film formed at a gas-liquid interface within pulmonary alveoli, the acid phospholipid is a component which stabilizes the film so formed, and both the fatty acid or its analogue and the lipoprotein are components which participate in the adsorption and spreading of the foregoing two components at the gas-liquid interface and promote the surface tension-reducing effect during the contraction of alveoli.

The choline phosphoglycerides which can be used in the surfactant of the invention include, for example, 1,2-diacylglycero-(3)-phosphocholines such as 1,2-dipalmitoylglycero-(3)-phosphocholine (also known as dipalmitoylphosphatidylcholine), 1,2-distearoylglycero-(3)-phosphocholine, 1-palmitoyl-2-stearoyl-glycero-(3)-phosphocholine, 1-stearoyl-2-palmitoyl-glycero-(3)-phosphocholine, etc.; 1-alkyl-2-acyl-glycero-(3)-phosphocholines such as 1-hexadecyl-2-palmitoylglycero-(3)-phosphocholine, 1-octadecyl-2-palmitoylglycero-(3)-phosphocholine, etc.; and 1,2-dialkylglycero-(3)-phosphocholines such as 1,2-dihexadecyl-glycero-(3)-phosphocholine, etc. As for these compounds, the existence of optical isomers due to the asymmetric carbon atom located at the 2-position of the glycerol residue is known. The choline phosphoglycerides used in the surfactant of the invention can be its D-isomer, L-isomer or so-called D,L-isomer (in which the D- and L-isomers are present as a mixture). In addition to the above-described simple compounds, mixtures of two or more 1,2-diacylglycero-(3)-phosphocholines with two acyl groups (preferably, two saturated acyl groups) having 14 to 24 carbon atoms can be used as choline phosphoglycerides. Moreover, such mixtures may be used in combination with the above-described simple compounds.

As the acid phospholipid, there may be used 1,2-diacylsn-glycero-(3)-phosphate (also known as L-α-phosphatidic acid), 1,2-diacyl-sn-glycero-(3)-phospho-L-serine (also known as phosphatidylserine), 1,2-diacyl-sn-glycero-(3)-phospho-sn-glycerol (also known as phosphatidylglycerol) and 1,2-diacyl-sn-glycero-(3)-phospho-(1)-L-myo-inositol (also known as phosphatidylinositol). In these compounds, the 1- and 2-positions may be substituted with the same or different acyl groups. These acyl groups preferably have 14 to 24 carbon atoms.

As the fatty acid or its analogue, there may be used free fatty acids, alkali metal salts of fatty acids, alkyl esters of fatty acids, glycerides of fatty acids, fatty acid amides and mixtures of two or more of the foregoing compounds, as well as fatty alcohols and aliphatic amines. The term "fatty acid or its analogue" as used herein is intended to comprehend fatty alcohols and aliphatic amines, too. Although useful free fatty acids include palmitic acid, stearic acid and oleic acid, palmitic acid is particularly preferred. Useful alkali metal salts of fatty acids include sodium palmitate and sodium stearate; useful alkyl esters of fatty acids include ethyl palmitate; useful glycerides of fatty acids include monopalmitin and monostearin; and useful fatty acid amides include palmitic acid amide. Useful fatty alcohols include hexadecyl alcohol and octadecyl alcohol; and useful aliphatic amines include hexadecylamine.

The above-described choline phosphoglycerides, acid phospholipids, and fatty acids or their analogues can be products isolated from animals or vegetables, semisynthetic products or chemically synthetic products. Moreover, commercially available products thereof can also be used.

The lipoprotein which can be used in the surfactant of the invention is suitably prepared from the lung of a mammal according to the procedure described hereinbelow.

[PROCEDURE OF THE PREPARATION OF LIPOPROTEIN]

(a) Lungs which have been excised from a mammal (such as cattle, horses, sheep, pigs or the like) are cut into fistsized lumps, freed of unnecessary blood vessels, windpipes, fat bodies, blood and the like, and then minced finely with a meat grinder. The resulting lung mince is brought into contact with physiological saline. This contact is effected, with stirring, at 0°–20° C. for 15–120 minutes. The mixture so prepared is filtered under pressure to obtain a crude extract.

(b) The above crude extract is centrifuged at 8,000–20,000 r.p.m. at 0°–10° C. to collect a crude sediment. The unnecessary lung fragments remaining in this crude sediment are removed by re-suspending the crude sediment in an electrolyte solution such as physiological saline or the like and centrifuging the resulting suspension at 500–2,000 r.p.m.

(c) The crude sediment thus obtained is suspended in water. To the resulting suspension is added sodium chloride so as to adjust its specific gravity to 1.10–1.20. The adjusted suspension is centrifuged at 5,000–13,000 r.p.m. at 0°–10° C. for 20–180 minutes to divide it into three layers. Then, the top layer comprising an emulsified scum layer is isolated.

(d) This top layer is suspended in water and the resulting suspension is dialyzed at 4°–10° C. for 6–24 hours through a cellophane membrane against water. The dialyzed suspension is lyophilized to obtain a crude dry product.

(e) This crude dry product is brought into contact with ethyl acetate or acetone at a temperature of −10° to 10° C., the amount of ethyl acetate or acetone used being equal to 20–200 times the weight of the crude dry product. The resulting mixture is stirred for 30–60 minutes. Thereafter, an insoluble material is separated and dried. This insoluble material is brought into contact with a chloroform-methanol mixture (with a volume ratio of 2:1) which is used in an amount equal to 80–200 times the weight of the insoluble material. The resulting mixture is stirred for 10–40 minutes and then filtered to obtain an extract filtrate.

(f) This extract filtrate is evaporated to dryness under reduced pressure and the resulting solid residue is dissolved in a chloroform-methanol mixture (with a volume ratio ranging from 2:1 to 4:1) which is used in an amount equal to 2–15 times, preferably 5–8 times, the weight of the solid residue. This solution is subjected to gel filtration by passing it through a column of a dextran gel, such as Sephadex LH-20, LH-60 or G-25 (Pharmacia Fine Chemicals Co.), to collect the void volume fraction. It is desirable that the dextran gel column to be used has previously been equilibrated with the same solvent mixture as is used to dissolve the solid residue. The size of the dextran gel column should be determined in such a way that the column bed volume is not less than 600 ml per gram of the solid residue to be subjected to gel filtration and the length of the dextran gel layer is not less than 50 cm, preferably not less than 80 cm, regardless of the column diameter.

(g) The above void volume fraction is evaporated to dryness under reduced pressure and the resulting residue is suspended in water. This suspension is lyophilized to obtain the desired lipoprotein in the form of a lightly yellowish-brown to yellowish-brown powder. Physicochemical properties of this lipoprotein are described hereinbelow.

[PHYSICOCHEMICAL PROPERTIES OF LIPOPROTEIN]

(i) Molecular Weight

When measured according to a method based on SDS-gel electrophoresis ("Methods for Experiments on Biological Membranes (Vol. 1)" as a special issue of "Tanpakushitsu-Kakusan-Koso", p. 230, 1974), the molecular weight of the lipoprotein is in the range of 30,000–38,000.

(ii) Chemical Proportion

The lipoprotein has a chemical proportion as shown in Table 1. In this table, the contents of various component parts are expressed as weight percentages based on the total weight of the lipoprotein. The content of phospholipid part was estimated by determining the phosphorus content of the lipoprotein according to the method of King et al. (Biochemical Journal, 26, 292, 1932) and multiplying the value thus obtained by 25. The content of protein part was determined according to the Dulley-Grieve method (Analytical Biochemistry, 64, 136, 1975) and expressed in terms of bovine serum albumin. The water content was determined according to Karl Fisher's method. The content of unknown component parts was determined by subtracting the sum of the above-described phospholipid part, protein part and water contents from the total weight of the lipoprotein.

TABLE 1

| Component part | Content [% (w/w)] |
| --- | --- |
| Phospholipid part | 47.9–70.2 |
| Protein part | 23.4–48.0 |
| Water | 1.8–5.0 |
| Unknown parts | 1.4–2.4 |

(iii) Optical Activity

The specific rotatory power $[\alpha]_D^{23}$ of the lipoprotein is in the range of −40° to −85°. Specifically, a sample of the lipoprotein was dissolved in a 1% aqueous solution of sodium dodecyl sulfate so as to give a concentration of 0.1%(w/v) and measured with an automatic polarimeter (Model DIP-180; Nihon Bunko Co., Ltd.).

(iv) Absorption Spectra

Infrared and ultraviolet absorption spectra of the lipoprotein are illustrated in FIGS. 4 and 5, respectively.

(v) Solubility

The lipoprotein is insoluble in chloroform, benzene, methanol, ethanol, dimethyl sulfoxide and water. At a concentration of 0.1%(w/v) or less, it is soluble in a chloroform-methanol mixture (with a volume ratio ranging from 2:1 to 4:1). It is also insoluble in a 0.1N aqueous solution of sodium hydroxide. Since the lipoprotein is insoluble in water and water-containing organic solvents, it cannot be determined whether the material is acidic, basic or neutral.

(vi) Color Reactions

The lipoprotein is positive to the xanthoprotein reaction. For the biuret reaction, however, it cannot be clearly judged whether the results are positive or negative.

Lipoproteins having the above-described physicochemical properties can be prepared not only from the lung of mammals but also from the amniotic fluid of human beings. In the latter case, an adequate amount of human amniotic fluid is collected and used in place of the crude extract in step(b) of the above-described preparation procedure. Thereafter, the same procedure may be followed.

The surfactant of the invention can be prepared by blending the choline phosphoglyceride, acid phospholipid, fatty acid or its analogue, and lipoprotein which have been described hereinabove. The proportions in which these components are blended should be determined so that the contents of the choline phosphoglyceride, acid phospholipid, fatty acid or its analogue, and lipoprotein are 50.6–85.0%(w/w), 4.5–37.6%(w/w), 4.6–24.6%(w/w) and 0.1–10.0%(w/w), respectively, based on the total dry weight of the final product. When these components are blended in other proportions than defined above, the resulting surfactant tends to show a reduction in surface activity.

The blending may be carried out by kneading together the above-described four components as such and then drying the resulting mixture, or by dissolving the four components in an organic solvent, mixing the resulting solutions, evaporating this mixture to dryness under reduced pressure, suspending the resulting residue in a suitable suspending medium, and then lyophilizing this suspension (the latter procedure is hereinafter referred to as the solution method). However, the solution method is preferred because the four components of the resulting surfactant can be uniformly dispersed in physiological saline with greater ease. In the solution method, a chloroform-methanol mixture (with a volume ratio ranging from 2:1 to 4:1) is suitable for use as the organic solvent for dissolving and mixing the four components. Although water or a water-ethanol mixture (with a volume ratio ranging from 4:1 to 20:1) is suitable for use as the suspending medium, the water-ethanol mixture is preferred. It is desirable to suspend the residue at 30°-60° C. for 5-60 minutes and preferably at 40°-50° C. for 15-30 minutes. From the nature of the solution method, the surfactant prepared by this method unavoidably contains a small amount of residual water. However, it is desirable to dry the surfactant to such an extent that the residual water content is not greater than 5.0%(w/w) based on the total weight of the surfactant. If the surfactant is dried to that extent, no residual ethanol is detectable even when a water-ethanol mixture is used.

Now, the surface activity and pharmacological properties of the surfactant so prepared are described in detail hereinbelow.

[I] SURFACE ACTIVITY (i) Surface Tension-Reducing Effect

The surfactant of the invention was added dropwise to the surface of physiological saline having a surface area of 54.0 cm$^2$, in an amount of 1.0 to 2.0 μg/cm$^2$. Then, according to Wilhelmy's method, the surface tension of the physiological saline was continuously measured at 37° C. while its surface area was being decreased and then increased between 54.0 cm$^2$ and 21.6 cm$^2$ over a period of 2-5 minutes (FIG. 1). For purposes of comparison, hysteresis curves were also obtained with a typical PC-PG mixture, a typical DPPC composition and TA-546 (FIGS. 2 and 3). The typical PC-PG mixture consisted of 90%(w/w) of phosphatidylcholine and 10%(w/w) of phosphatidylglycerol, and the typical DPPC composition consisted of 82%(w/w) of dipalmitoylphosphatidylcholine and 18%(w/w) of hexadecyl alcohol. The results thus obtained are shown in Table 2. The initial surface tension of phyisological saline was 70.5 dynes/cm.

TABLE 2

|  | Highest surface tension (dynes/cm) | Lowest surface tension (dynes/cm) |
| --- | --- | --- |
| Surfactant of the invention | 18.5-35.0 | 0.4-10.0 |
| PC-PG mixture | 48.1 | 16.2 |
| DPPC composition | 61.2 | 8.3 |
| TA-546 | 32.3-47.5 | 2.0-12.2 |

It can be seen from Table 2 that the surfactant of the invention reduced the surface tension of physiological saline by factors of 176.3 at a maximum and 2.0 at a minimum.

(ii) Spreadability Over a Gas-Liquid Interface

The surfactant of the invention was added dropwise to the surface of physiological saline in an amount of 0.8 to 1.5 μg. As soon as the surfactant was added, changes of its surface tension with time were measured according to the vertical plate method. The measurement was made at 37° C. The results thus obtained are shown in Table 3. In this table, the results obtained in the same manner with a typical PC-PG mixture, a typical DPPC composition and TA-546 are also given. The typical PC-PG mixture and DPPC composition had the same chemical compositions as described above. As used herein, the term "equilibration time" means the time elapsed between the addition of the sample and the attainment of a constant value for surface tension and the term "equilibrium surface tension" means the constant value so attained.

TABLE 3

|  | Equilibration time (seconds) | Equilibrium surface tension (dynes/cm) |
| --- | --- | --- |
| Surfactant of the invention | 30-100 | 23.9-35.0 |
| PC-PG mixture | 180 | 55.5 |
| DPPC composition | 125 | 64.2 |
| TA-546 | About 120 | 26.3-48.1 |

As is evident from Table 3, the surfactant of the invention were found to form a kind of film at the gas-liquid interface in a time as short as 30-100 seconds and thereby reduce the surface tension.

(iii) Adsorbability to a Gas-Liquid Interface

The surfactant of the invention was suspended in physiological saline at 37° C. to prepare a suspension containing 20-100 μg of the surfactant per milliliter of the saline. Thus, the adsorption rate of the suspended surfactant to the gas-liquid interface was estimated according to the method of King et al. (American Journal of Physiology, 223, 715, 1972). Specifically, as soon as the suspension was prepared, changes of its surface tension with time were measured. The surface tension began to decrease from an initial value of 70.5 dynes/cm and, after 30-120 seconds, reached a constant value in the range of 22.5-40.1 dynes/cm. This indicates that, within 30-120 seconds after being suspended, the surfactant of the invention rose and became adsorbed to the gas-liquid interface and formed a kind of film having strong surface activity. When TA-546 was tested in the same manner, the time required for the surface tension to reach a constant value was as long as about 150 seconds and the constant value was in the range of 33.2-55.0 dynes/cm.

[II] PHARMACOLOGICAL PROPERTIES (i) Acute Toxicity

The acute toxicity of the surfactant of the invention was tested by administering them orally or intraperitoneally to 5-weeks-old male ICR mice and Wistar rats. For mice, the oral and intraperitoneal LD$_{50}$ values were 2.5-10.0 g/kg and 1.4-5.0 g/kg, respectively. For rats, the oral and intraperitoneal LD$_{50}$ values were 1.3-5.0 g/kg and 1.2-2.6 g/kg, respectively.

(ii) Subacute Toxicity

The surfactant of the invention was administered intraperitoneally to mature Wistar rats in a daily dose of 280–600 mg/kg for one month. No significant change in body weight was noted. Moreover, visual observation and histological examination of principal organs revealed no abnormalities.

(iii) Alveolar Volume-Maintaining Effect

Using 7 rabbit fetuses removed after 27 days of gestation, alveolar volume changes at decreasing endotracheal pressures were measured. Specifically, the neck of each fetus was incised to expose the trachea, to which a water manometer was connected directly. Beginning at 5 minutes after treatment with the surfactant of the invention, the alveolar volume was measured continuously. The endotracheal pressure was varied by means of an independently-acting 2-channel syringe pump (No. 940; Harvard Inc.). The treatment with the surfactant of the invention was carried out by preparing a 1.0–6.0%(w/v) suspension of the surfactant in physiological saline and instilling 0.05–0.5 ml of the suspension directly into the trachea. In a control group, measurements were made in the same manner except that the suspension of the surfactant of the invention was replaced by physiological saline. The alveolar volume was expressed as the number of milliliters per kilogram of body weight. The results thus obtained are shown in Table 4. In this table, the results obtained in the same manner with a typical DPPC composition (having the same chemical composition as described above) and TA-546 are also given.

TABLE 4

| Endotracheal pressure (cm $H_2O$) | Alveolar volume (ml/kg) | | | |
|---|---|---|---|---|
| | Control group | Group treated with the Surfactant of the invention | Group treated with DPPC composition | Group treated with TA-546 |
| 30 | 12 ± 5 | 77 ± 11 | 25 ± 5 | 55 ± 2 |
| 25 | 12 ± 5 | 77 ± 13 | 26 ± 4 | 49 ± 3 |
| 20 | 11 ± 4 | 75 ± 10 | 22 ± 5 | 47 ± 3 |
| 15 | 10 ± 4 | 70 ± 9 | 20 ± 3 | 44 ± 3 |
| 10 | 5 ± 4 | 60 ± 9 | 17 ± 4 | 39 ± 4 |
| 5 | 2 ± 2 | 45 ± 10 | 10 ± 3 | 25 ± 3 |
| 0 | 0 | 23 ± 9 | 3 ± 2 | 17 ± 4 |

(iv) Improvement of Respiratory Function in a Model for RDS

The respiratory function-improving capacity of the surfactant of the invention was tested on 10- to 12-weeks-old guinea pigs suffering from RDS experimentally induced by lavage of the lungs. In a treatment group, 8 RDS guinea pigs prepared in the above-described manner were placed under controlled respiration and allowed to stand for 3 hours. Then, the surfactant of the invention was administered in a dose of 40–100 mg/kg and the animals were allowed to stand for an additional 3 hours. Thereafter, the animals were killed by exsanguination and their alveolar volume was measured. In a normal group, 10 normal guinea pigs of the same age were directly killed by exsanguination and their alveolar volume was measured. In a control group, 8 RDS guinea pigs were placed under controlled respiration and allowed to stand for 6 hours. Thereafter, the animals were killed by exsanguination and their alveolar volume was measured. The prepartion of RDS guinea pigs and the application of controlled respiration were done according to the methods of Lachmann et al. (Acta Anesthesiologica Scandinavica, 24,231, 1980). The treatment with the surfactant of the invention was carried out by preparing a 1.0–6.0%(w/v) suspension of the surfactant in physiological saline and instilling the suspension directly into the trachea. The alveolar volume was measured in substantially the same manner as described above. The results thus obtained are shown in Table 5.

TABLE 5

| Endotracheal pressure (cm $H_2O$) | Alveolar volume (ml/kg) | | |
|---|---|---|---|
| | Control group | Group treated with the surfactant of the invention | Normal group |
| 30 | 7.2 ± 3.3 | 17.7 ± 3.4 | 17.5 ± 3.1 |
| 25 | 6.8 ± 2.8 | 16.8 ± 3.5 | 16.3 ± 2.8 |
| 20 | 5.2 ± 2.1 | 15.9 ± 3.2 | 16.0 ± 2.7 |
| 15 | 4.6 ± 1.7 | 14.3 ± 3.0 | 14.4 ± 2.5 |
| 10 | 3.8 ± 1.6 | 13.2 ± 2.7 | 13.6 ± 2.0 |
| 5 | 1.5 ± 0.9 | 10.4 ± 2.3 | 10.2 ± 1.6 |
| 0 | 0 | 5.3 ± 1.7 | 5.2 ± 1.6 |

It can be seen from Table 5 that the surfactant of the invention almost completely restored the respiratory function to normal.

(V) Improvement of Respiratory Function in RDS Arising from Septicemia

The respiratory function-improving capacity of the surfactant of the invention was tested on mature rabbits suffering from septicemia which had been induced by intraperitoneal inoculation of Escherichia coli and further complicated with RDS. A total of four groups, each of which consisted of 6 rabbits prepared in the above-described manner, were used and one of them underwent no treatment. The other groups were treated with kanamycin sulfate alone, the surfactant of the invention alone, and a combination of kanamycin sulfate and the surfactant of the invention, respectively. The rabbits with RDS arising from septicemia were prepared and the degree of lung injury was evaluated according to the methods of Cuevas et al. (Archives of Surgery, 104, 319, 1972), and the circulating titer of endotoxin in blood was determined according to the method of Reinhold et al. (Proceedings of the Society for Experimental Biology and Medicine, 137, 334, 1971). The treatment with the surfactant of the invention and/or kanamycin sulfate was carried out within 24 hours before and after the onset of RDS. The surfactant of the invention was instilled 1–6 times into the airway in a dose of 50–100 mg/kg for each treatment, while 80–150 mg/kg of kanamycin sulfate was intramuscularly injected in 2–8 divided doses. Two days after treatment, the animals were examined for survival and the degree of lung injury. The results thus obtained are shown in Table 6. As for the animals that had died, the degree of lung injury observed immediately before their death was employed. The degree of lung injury becomes severer as the value increases.

TABLE 6

| Group | Rabbit No. | Circulating titer (μg/ml) | Degree of lung injury | Survival |
|---|---|---|---|---|
| Untreated group | 1 | 0.40 | 2 | No |
| | 2 | 0.50 | 3 | No |
| | 3 | 0.20 | 2 | No |
| | 4 | 0.40 | 3 | No |
| | 5 | 1.00 | 2 | No |

TABLE 6-continued

| Group | Rabbit No. | Circulating titer (μg/ml) | Degree of lung injury | Survival |
|---|---|---|---|---|
| | 6 | 0.40 | 3 | No |
| Group treated with kanamycin sulfate alone | 7 | 0.10 | 2 | No |
| | 8 | 0.20 | 3 | No |
| | 9 | 0.01 | 1 | Yes |
| | 10 | 0.02 | 0 | Yes |
| | 11 | 0.00 | 0 | Yes |
| | 12 | 0.05 | 2 | No |
| Group treated with the surfactant of the invention alone | 13 | 0.10 | 0 | Yes |
| | 14 | 1.00 | 3 | No |
| | 15 | 0.02 | 0 | Yes |
| | 16 | 0.40 | 2 | No |
| | 17 | 0.05 | 0 | Yes |
| | 18 | 0.20 | 1 | No |
| Group treated with kanamycin sulfate and the surfactant of the invention | 19 | 0.01 | 0 | Yes |
| | 20 | 0.05 | 1 | Yes |
| | 21 | 0.02 | 1 | Yes |
| | 22 | 0.00 | 0 | Yes |
| | 23 | 0.05 | 0 | Yes |
| | 24 | 0.20 | 2 | No |

It can be seen from Table 6 that the surfactant of the invention brought about a significant improvement in respiratory function.

Judging from the surface activity and pharmacological properties described in detail hereinabove, pharmaceutical compositions containing the surfactant of the invention as active ingredient can be regarded as useful remedies for RDS.

The pharmaceutical compositions provided by the present invention for the treatment of RDS contain the surfactant of the invention in such an amount that each unit dosage provides 40–500 mg of the surfactant for premature infants or 400–4,000 mg of the surfactant for adults. In administering these pharmaceutical compositions, the above-described unit dosage is suspended in water or physiological saline so as to give a concentration of 1.0–6.0%(w/v) and the resulting suspension is instilled or sprayed into the airway of the patient. For premature infants, the treatment should be carried out within 72 hours after their birth, while for adults, the treatment should be carried out within 120 hours before or after the onset of respiratory disturbances. The preferred number of treatments is 1–4 for premature infants and 1–10 for adults. The above-described dosage, method of administration, and number of treatments may be suitably modified depending on the symptoms of the patient and the concomitantly used therapy. For adults, it is desirable to use the pharmaceutical composition of the invention in combination with suitable drugs for the basic disease, such as antibiotics, antidotes and the like.

The pharmaceutical compositions of the invention may further contain suitable additives (e.g., stabilizers, preservatives, osmotic pressure regulators, buffering agents, suspending agents and the like) and germicides as required. Preferably, the pharmaceutical compositions of the invention are in the form of a liquid or a powder which is intended for suspension prior to use. The pharmaceutical compositions of the invention are charged into hermetically sealed containers such as vials, ampules or the like, and thereby stored aseptically.

The present invention is further illustrated by the following examples.

REFERENCE EXAMPLE 1

(Preparation of Lipoprotein from Cattle Lungs)

(a) Lungs (128.3 kg) excised from cattle were washed with water to remove any blood and other contaminants adhering thereto. Then, the lungs were cut into fist-sized lumps and freed of unnecessary blood vessels, windpipes and the like with the aid of scissors. These lumps were finely minced with a meat grinder to obtain 120.1 kg of lung mince. This lung mince was mixed with 490 liters of physiological saline. The resulting mixture was stirred at 4° C. for 100 minutes, placed in a filter bag, and filtered under pressure to obtain 470 liters of a crude extract.

(b) The above crude extract was centrifuged at 10,000 r.p.m. to collect a crude sediment. This crude sediment was re-suspended in 100 liters of physiological saline and then centrifuged at 2,000 r.p.m. for 10 minutes to precipitate off any residual tissue fragments and the like. The suspension obtained as the top layer was centrifuged again at 10,000 r.p.m. to collect a crude sediment.

(c) The crude sediment thus obtained was suspended in 85 liters of water. To the resulting suspension was added 25.7 kg of sodium chloride so as to adjust its specific gravity to approximately 1.20. The adjusted suspension was centrifuged at 10,000 r.p.m. at 0° C. for 50 minutes to divide it into three layers. The top layer comprising an emulsified scum layer was isolated.

(d) The isolated top layer was suspended in distilled water and the resulting suspension was dialyzed through a cellophane membrane against distilled water. Thereafter, the dialyzed suspension was lyophilized to obtain 960 g of a crude dry product.

(e) To this crude dry product was added 48 liters of cold ethyl acetate at 5° C. The resulting mixture was mixed for 45 minutes and then filtered under reduced pressure to separate an insoluble material. After this insoluble material was dried, 28 liters of a solvent mixture consisting of chloroform and methanol (in a volume ratio of 2:1) was added thereto. The resulting mixture was stirred for 30 minutes and then filtered through filter paper to obtain an extract filtrate. To the filtration residue was added 28 liters of the same solvent mixture. The resulting mixture was stirred for 30 minutes and then filtered through a filter paper to obtain a secondary extract filtrate. This procedure was repeated once more to obtain a tertiary extract filtrate. The combined volume of the extract filtrate thus obtained was 82 liters.

(f) This extracted filtrate was evaporated to dryness under reduced pressure, so that 160.4 g of a solid residue was obtained. The resulting solid residue was divided into six 25.0 g portions and treated as follows: Each 25.0 g portion of the solid residue was dissolved in 170 ml of a chloroform-methanol mixture (with a volume ratio of 2:1). The resulting solution was added to a column of Sephadex LH-20 (15.5 cm in diameter and 90 cm in length; 17.0 liters in column bed volume) which had been equilibrated with the same solvent mixture, and then eluted with the same solvent mixture at a flow rate of 5 ml/min to collect the void volume fraction. The combined volume of the void volume fraction obtained by repeating this gel filtration procedure six times was 6,480 ml. When a sterility test was made on a small sample of this fraction, it was found to be sterile. Accordingly, all subsequent operations were carried out under sterile conditions.

(g) The void volume fraction was evaporated to dryness under reduced pressure and the resulting residue was suspended in sterilized water. This suspension was lyophilized to obtain a yield of 8.3 g of lipoprotein in the form of a lightly yellowish-brown powder. It had a molecular weight of 34,000 and a specific rotatory power $[\alpha]_D^{23}$ of $-69°$. When its chemical proportion was analyzed, the contents of phospholipid part, protein part, water and unknown component parts were found to be 62.1%(w/w), 31.3%(w/w), 4.6%(w/w) and 2.0%(w/w), respectively.

REFERENCE EXAMPLE 2

(Preparation of Lipoprotein from Pig Lungs)

Lungs (36 kg) excised from pigs were treated in the same manner as described in step (a) of Reference Example 1 to obtain 33.5 kg of lung mince. This lung mince was mixed with 168 liters of physiological saline. The resulting mixture was stirred at 10° C. for 30 minutes, placed in a filter bag, and filtered under pressure to obtain 145 liters of a crude extract.

(b) The above crude extract was centrifuged at 14,000 r.p.m. to collect a crude sediment. This crude sediment was re-suspended in 20 liters of physiological saline and then centrifuged at 1,000 r.p.m. at 4° C. to precipitate off any residual tissue fragments and the like. The suspension obtained as the top layer was centrifuged again at 13,000 r.p.m. to collect a crude sediment.

(c) The crude sediment thus obtained was suspended in 26 liters of water. To the resulting suspension was added 5.8 kg of sodium chloride so as to adjust its specific gravity to approximately 1.15. The adjusted suspension was centrifuged at 8,000 r.p.m. at 4° C. for 30 minutes and the top layer comprising an emulsified scum layer was isolated.

(d) The isolated top layer was suspended in distilled water and the resulting suspension was dialyzed through a cellophane membrane against distilled water. Thereafter, the dialyzed suspension was lyophilized to obtain 163 g of a crude dry product.

(e) To this crude dry product was added 15 liters of acetone at 6° C. The resulting mixture was mixed for 30 minutes and then filtered through filter paper to separate an insoluble material. After this insoluble material was dried, 23 liters of a chloroform-methanol mixture (with a volume ratio of 2:1) was brought into contact therewith. The resulting mixture was stirred for 20 minutes and then filtered through filter paper to obtain 22 liters of an extract filtrate.

(f) This extract filtrate was evaporated to dryness under reduced pressure, so that 46.2 g of a solid residue was obtained. A 20.0 g portion of the solid residue was dissolved in 120 ml of a chloroform-methanol mixture (with a volume ratio of 3:1). The resulting solution was added to a column of Sephadex LH-20 (15.5 cm in diameter and 88 cm in length; 16.6 liters in column bed volume) which had been equilibrated with the same solvent mixture, and then eluted with the same solvent mixture at a flow rate of 3 ml/min to collect 910 ml of the void volume fraction. When a sterility test was made on a small sample of this fraction, it was found to be sterile. Accordingly, all subsequent operations were carried out under sterile conditions.

(g) The above void volume fraction was evaporated to dryness under reduced pressure and the resulting residue was suspended in sterilized water. This suspension was lyophilized to obtain a yield of 1.1 g of lipoprotein in the form of a yellowish-brown powder. It had a molecular weight of 32,000 and a specific rotatory power $[\alpha]_D^{23}$ of $-51°$. When its chemical proportion was analyzed, the contents of phospholipid part, protein part, water and unknown component parts were found to be 69.2%(w/w), 26.4%(w/w), 3.0%(w/w) and 1.4%(w/w), respectively.

EXAMPLE 1

After being sterilized, 6.58 g of 1,2-dipalmitoyl-glycero-(3)-phosphocholine, 2.19 g of 1,2-diacyl-sn-glycero-(3)-phospho-sn-glycerol (with acyl groups having 14 to 24 carbon atoms; Sigma Chemicals Co.), 1.10 g of palmitic acid and 0.13 g of the lipoprotein prepared in Reference Example 1 were added to and dissolved in 10.0 liters of a chloroform-methanol mixture (with a volume ratio of 2:1) at room temperature. This solution was evaporated to dryness under reduced pressure and the resulting residue was suspended in 1.0 liter of a water-ethanol mixture (with a volume ratio of 9:1) at 45° C. over a period of 20 minutes. This suspension was frozen at $-40°$ C. and dried at a vacuum of 75–90 μmHg for 24 hours to obtain a yield of 10.33 g of surfactant in the form of a white powder. No residual ethanol was detected in this powder. Accordingly, the contents of 1,2-dipalmitoylglycero-(3)-phosphocholine, 1,2-diacyl-sn-glycero-(3)-phospho-sn-glycerol, palmitic acid, lipoprotein and water were 63.7%(w/w), 21.2%(w/w), 10.6%(w/w), 1.3%(w/w) and 3.2%(w/w), respectively, based on the total weight of the surfactant. Properties of the surfactant thus obtained were as follows.

(i) Surface Tension-Reducing Effect

Highest surface tension: 21.2 dynes/cm.
Lowest surface tension: 1.2 dynes/cm.

(ii) Spreadability Over a Gas-Liquid Interface

Equilibration time: 30 seconds.
Equilibrium surface tension: 28.9 dynes/cm.

(iii) Alveolar Volume-Maintaining Effect

Alveolar volume (at 5 cmH$_2$O): 53 ml/kg.

EXAMPLE 2

After being sterilized, 336.5 mg of 1,2-dipalmitoyl-glycero-(3)-phosphocholine, 112.0 mg of 1,2-diacyl-sn-glycero-(3)-phospho-sn-glycerol (with acyl groups having 14 to 24 carbon atoms; Sigma Chemicals Co.), 45.0 mg of palmitic acid and 6.5 mg of the lipoprotein prepared in Reference Example 1 were added to and dissolved in 520 ml of a chloroform-methanol mixture (with a volume ratio of 4:1). The solvent of this solution was distilled off under reduced pressure and the resulting residue was suspended in 200 ml of a water-ethanol mixture (with a volume ratio of 15:1) at 40° C. over a period of 30 minutes. This suspension was frozen at $-50°$ C. and dried at a vacuum of 70–100 μmHg for 36 hours to obtain a yield of 514.5 mg of surfactant in the form of a white powder. Since no ethanol was detected in this powder, the contents of 1,2-dipalmitoylglycero-(3)-phosphocholine, 1,2-diacyl-sn-glycero-(3)-phospho-sn-glycerol, palmitic acid, lipoprotein and water were 65.4%(w/w), 21.8%(w/w), 8.7%(w/w), 1.3%(w/w) and 2.8%(w/w), respectively, based on the total weight of the surfactant. Properties of the surfactant thus obtained were as follows.

(i) Surface Tension-Reducing Effect

Highest surface tension: 26.5 dynes/cm.
Lowest surface tension: 1.9 dynes/cm.

(ii) Spreadability Over a Gas-Liquid Interface

Equilibration time: 35 seconds.
Equilibrium surface tension: 27.1 dynes/cm.

(iii) Alveolar Volume-Maintaining Effect

Alveolar volume (at 5 cmH$_2$O): 55 ml/kg.

In the following Examples 3–5, surfactants were prepared by using 112.0 mg of 1,2-diacyl-sn-glycero-(3)-phospho-L-serine (with acyl groups having 14 to 24 carbon atoms; Sigma Chemicals Co.), 1,2-diacyl-sn-glycero-(3)-phospho-(1)-L-myo-inositol (with acyl groups having 14 to 24 carbon atoms; Serdary Research Laboratories Inc.) or 1,2-diacyl-sn-glycero-(3)-phosphate (with acyl groups having 14 to 24 carbon atoms; Serdary Research Laboratories Inc.) in place of the 1,2-diacyl-sn-glycero-(3)-phospho-sn-glycerol (112.0 mg). The amounts of the three other components and the preparation procedure were all the same as described above.

EXAMPLE 3

[Chemical Composition]

| Component | Content |
| --- | --- |
| 1,2-Dipalmitoylglycero-(3)-phosphocholine | 65.4% (w/w) |
| 1,2-Diacyl-sn-glycero-(3)-phospho-L-serine | 21.8% (w/w) |
| Palmitic acid | 8.7% (w/w) |
| Lipoprotein | 1.3% (w/w) |
| Water | 2.8% (w/w) |

[Yield and Appearance]

514.6 mg; white powder.

(i) Surface Tension-Reducing Effect

Highest surface tension: 28.2 dynes/cm.
Lowest surface tension: 1.6 dynes/cm.

(ii) Spreadability Over a Gas-Liquid Interface

Equilibration time: 35 seconds.
Equilibrium surface tension: 27.4 dynes/cm.

(iii) Alveolar Volume-Maintaining Effect

Alveolar volume (at 5 cmH$_2$O): 54 ml/kg.

EXAMPLE 4

[Chemical Composition]

| Component | Content |
| --- | --- |
| 1,2-Dipalmitoylglycero-(3)-phosphocholine | 66.2% (w/w) |
| 1,2-Diacyl-sn-glycero-(3)-phospho-(1)-L-myo-inositol | 22.0% (w/w) |
| Palmitic acid | 8.8% (w/w) |
| Lipoprotein | 1.3% (w/w) |
| Water | 1.7% (w/w) |

[Yield and Appearance]

508.5 mg; white powder.

(i) Surface Tension-Reducing Effect

Highest surface tension: 35.0 dynes/cm.
Lowest surface tension: 6.3 dynes/cm.

(ii) Spreadability Over a Gas-Liquid Interface

Equilibration time: 100 seconds.
Equilibrium surface tension: 35.0 dynes/cm.

(iii) Alveolar Volume-Maintaining Effect

Alveolar volume (at 5 cmH$_2$O): 35 ml/kg.

EXAMPLE 5

[Chemical Composition]

| Component | Content |
| --- | --- |
| 1,2-Dipalmitoylglycero-(3)-phosphocholine | 64.7% (w/w) |
| 1,2-Diacyl-sn-glycero-(3)-phosphate | 21.5% (w/w) |
| Palmitic acid | 8.7% (w/w) |
| Lipoprotein | 1.3% (w/w) |
| Water | 3.8% (w/w) |

[Yield and Appearance]

520.0 mg; pale-yellow powder.

(i) Surface Tension-Reducing Effect

Highest surface tension: 28.1 dynes/cm.
Lowest surface tension: 5.9 dynes/cm.

(ii) Spreadability Over a Gas-Liquid Interface

Equilibration time: 85 seconds.
Equilibrium surface tension: 30.3 dynes/cm.

(iii) Alveolar Volume-Maintaining Effect

Alveolar volume (at 5 cmH$_2$O): 42 ml/kg.

EXAMPLE 6

After being sterilized, 408.0 mg of 1,2-dipalmitoylglycero-(3)-phosphocholine, 126.0 mg of 1,2-diacyl-sn-glycero-(3)-phospho-sn-glycerol (with acyl groups having 14 to 24 carbon atoms; Sigma Chemicals Co.), 54.0 mg of palmitic acid and 12.0 mg of the lipoprotein prepared in Reference Example 1 were added to and dissolved in 610 ml of a chloroform-methanol mixture (with a volume ratio of 3:1). This solution was evaporated to dryness under reduced pressure and the resulting residue was suspended in 300 ml of a water-ethanol mixture (with a volume ratio of 10:1) at 50° C. over a period of 15 minutes. This suspension was frozen at −60° C. and dried at a vacuum of 50–120 μmHg for 40 hours to obtain a surfactant.

[Chemical Composition]

| Component | Content |
| --- | --- |
| 1,2-Dipalmitoylglycero-(3)-phosphocholine | 65.3% (w/w) |
| 1,2-Diacyl-sn-glycero-(3)-phospho-sn-glycerol | 20.2% (w/w) |
| Palmitic acid | 8.6% (w/w) |
| Lipoprotein | 1.9% (w/w) |
| Water | 4.0% (w/w) |

[Yield and Appearance]

625.2 mg; white powder.

(i) Surface Tension-Reducing Effect

Highest surface tension: 24.2 dynes/cm.
Lowest surface tension: 1.8 dynes/cm.

(ii) Spreadability Over a Gas-Liquid Interface

Equilibration time: 40 seconds.
Equilibrium surface tension: 29.2 dynes/cm.

(iii) Alveolar Volume-Maintaining Effect

Alveolar volume (at 5 cmH$_2$O): 51 ml/kg.

In addition, eleven other surfactants in Examples 7-17 below were prepared in all the same manner as described above, except that 54.0 mg of another fatty acid or its analogue was used in place of the palmitic acid (54.0 mg).

EXAMPLE 7

[Chemical Composition]

| Component | Content |
| --- | --- |
| 1,2-Dipalmitoylglycero-(3)-phosphocholine | 65.7% (w/w) |
| 1,2-Diacyl-sn-glycero-(3)-phospho-sn-glycerol | 20.3% (w/w) |
| Stearic acid | 8.7% (w/w) |
| Lipoprotein | 1.9% (w/w) |
| Water | 3.4% (w/w) |

[Yield and Appearance]

621.0 mg; white powder.

(i) Surface Tension-Reducing Effect

Highest surface tension: 23.8 dynes/cm.
Lowest surface tension: 0.8 dynes/cm.

(ii) Spreadability Over a Gas-Liquid Interface

Equilibration time: 70 seconds.
Equilibrium surface tension: 30.2 dynes/cm.

(iii) Alveolar Volume-Maintaining Effect

Alveolar volume (at 5 cmH$_2$O): 48 ml/kg.

EXAMPLE 8

[Chemical Composition]

| Component | Content |
| --- | --- |
| 1,2-Dipalmitoylglycero-(3)-phosphocholine | 65.5% (w/w) |
| 1,2-Diacyl-sn-glycero-(3)-phospho-sn-glycerol | 20.2% (w/w) |
| Oleic acid | 8.7% (w/w) |
| Lipoprotein | 1.9% (w/w) |
| Water | 3.7% (w/w) |

[Yield and Appearance]

622.8 mg; pale-yellow powder.

(i) Surface Tension-Reducing Effect

Highest surface tension: 28.5 dynes/cm.
Lowest surface tension: 1.8 dynes/cm.

(ii) Spreadability Over a Gas-Liquid Interface

Equilibration time: 95 seconds.
Equilibrium surface tension: 24.2 dynes/cm.

(iii) Alveolar Volume-Maintaining Effect

Alveolar volume (at 5 cmH$_2$O): 46 ml/kg.

EXAMPLE 9

[Chemical Composition]

| Component | Content |
| --- | --- |
| 1,2-Dipalmitoylglycero-(3)-phosphocholine | 66.5% (w/w) |
| 1,2-Diacyl-sn-glycero-(3)-phospho-sn-glycerol | 20.5% (w/w) |
| Sodium palmitate | 8.8% (w/w) |
| Lipoprotein | 2.0% (w/w) |
| Water | 2.2% (w/w) |

[Yield and Appearance]

613.8 mg; white powder (i) Surface Tension-Reducing Effect

Highest surface tension: 26.5 dynes/cm.
Lowest surface tension: 1.9 dynes/cm.

(ii) Spreadability Over a Gas-Liquid Interface

Equilibration time: 35 seconds.
Equilibrium surface tension: 27.1 dynes/cm.

(iii) Alveolar Volume-Maintaining Effect

Alveolar volume (at 5 cmH$_2$O): 50 ml/kg.

EXAMPLE 10

[Chemical Composition]

| Component | Content |
| --- | --- |
| 1,2-Dipalmitoylglycero-(3)-phosphocholine | 66.2% (w/w) |
| 1,2-Diacyl-sn-glycero-(3)-phospho-sn-glycerol | 20.4% (w/w) |
| Sodium stearate | 8.8% (w/w) |
| Lipoprotein | 1.9% (w/w) |
| Water | 2.7% (w/w) |

[Yield and Appearance]

616.7 mg; white powder.

(i) Surface Tension-Reducing Effect

Highest surface tension: 32.0 dynes/cm.
Lowest surface tension: 3.8 dynes/cm.

(ii) Spreadability Over a Gas-Liquid Interface

Equilibration time: 85 seconds.
Equilibrium surface tension: 29.8 dynes/cm.

(iii) Alveolar Volume-Maintaining Effect

Alveolar volume (at 5 cmH$_2$O): 43 ml/kg.

EXAMPLE 11

[Chemical Composition]

| Component | Content |
| --- | --- |
| 1,2-Dipalmitoylglycero-(3)-phosphocholine | 66.8% (w/w) |
| 1,2-Diacyl-sn-glycero-(3)-phospho-sn-glycerol | 20.6% (w/w) |
| Ethyl palmitate | 8.8% (w/w) |
| Lipoprotein | 2.0% (w/w) |
| Water | 1.8% (w/w) |

[Yield and Appearance]

610.8 mg; white powder.

(i) Surface Tension-Reducing Effect

Highest surface tension: 24.3 dynes/cm.
Lowest surface tension: 1.1 dynes/cm.

(ii) Spreadability Over a Gas-Liquid Interface

Equilibration time: 65 seconds.
Equilibrium surface tension: 26.5 dynes/cm.

(iii) Alveolar Volume-Maintaining Effect

Alveolar volume (at 5 cmH$_2$O): 48 ml/kg.

EXAMPLE 12

[Chemical Composition]

| Component | Content |
|---|---|
| 1,2-Dipalmitoylglycero-(3)-phosphocholine | 66.4% (w/w) |
| 1,2-Diacyl-sn-glycero-(3)-phospho-sn-glycerol | 20.5% (w/w) |
| Monopalmitin | 8.8% (w/w) |
| Lipoprotein | 2.0% (w/w) |
| Water | 2.3% (w/w) |

[Yield and Appearance]

614.4 mg; white powder (i) Surface Tension-Reducing Effect

Highest surface tension: 25.5 dynes/cm.
Lowest surface tension: 3.7 dynes/cm.

(ii) Spreadability Over a Gas-Liquid Interface

Equilibration time: 80 seconds.
Equilibrium surface tension: 28.8 dynes/cm.

(iii) Alveolar Volume-Maintaining Effect

Alveolar volume (at 5 cmH$_2$O): 41 ml/kg.

EXAMPLE 13

[Chemical Composition]

| Component | Content |
|---|---|
| 1,2-Dipalmitoylglycero-(3)-phosphocholine | 66.3% (w/w) |
| 1,2-Diacyl-sn-glycero-(3)-phospho-sn-glycerol | 20.5% (w/w) |
| Monostearin | 8.8% (w/w) |
| Lipoprotein | 1.9% (w/w) |
| Water | 2.5% (w/w) |

[Yield and Appearance]

615.6 mg; white powder.

(i) Surface Tension-Reducing Effect

Highest surface tension: 33.9 dynes/cm.
Lowest surface tension: 8.2 dynes/cm.

(ii) Spreadability Over a Gas-Liquid Interface

Equilibration time: 95 seconds.
Equilibrium surface tension: 35.0 dynes/cm.

(iii) Alveolar Volume-Maintaining Effect

Alveolar volume (at 5 cmH$_2$O): 36 ml/kg.

EXAMPLE 14

[Chemical Composition]

| Component | Content |
|---|---|
| 1,2-Dipalmitoylglycero-(3)-phosphocholine | 65.4% (w/w) |
| 1,2-Diacyl-sn-glycero-(3)-phospho-sn-glycerol | 20.2% (w/w) |
| Palmitic acid amide | 8.7% (w/w) |
| Lipoprotein | 1.9% (w/w) |
| Water | 3.8% (w/w) |

[Yield and Appearance]

624.0 mg; white powder.

(i) Surface Tension-Reducing Effect

Highest surface tension: 27.8 dynes/cm.
Lowest surface tension: 2.2 dynes/cm.

(ii) Spreadability Over a Gas-Liquid Interface

Equilibration time: 55 seconds.
Equilibrium surface tension: 29.8 dynes/cm.

(iii) Alveolar Volume-Maintaining Effect

Alveolar volume (at 5 cmH$_2$O): 49 ml/kg.

EXAMPLE 15

[Chemical Composition]

| Component | Content |
|---|---|
| 1,2-Dipalmitoylglycero-(3)-phosphocholine | 67.3% (w/w) |
| 1,2-Diacyl-sn-glycero-(3)-phospho-sn-glycerol | 20.8% (w/w) |
| Hexadecyl alcohol | 8.9% (w/w) |
| Lipoprotein | 2.0% (w/w) |
| Water | 1.0% (w/w) |

[Yield and Appearance]

606.0 mg; white powder.

(i) Surface Tension-Reducing Effect

Highest surface tension: 33.5 dynes/cm.
Lowest surface tension: 0.7 dynes/cm.

(ii) Spreadability Over a Gas-Liquid Interface

Equilibration time: 75 seconds.
Equilibrium surface tension: 32.2 dynes/cm.

(iii) Alveolar Volume-Maintaining Effect

Alveolar volume (at 5 cmH$_2$O): 45 ml/kg.

EXAMPLE 16

[Chemical Composition]

| Component | Content |
|---|---|
| 1,2-Dipalmitoylglycero-(3)-phosphocholine | 66.0% (w/w) |
| 1,2-Diacyl-sn-glycero-(3)-phospho-sn-glycerol | 20.4% (w/w) |
| Hexadecylamine | 8.7% (w/w) |
| Lipoprotein | 2.0% (w/w) |
| Water | 2.9% (w/w) |

[Yield and Appearance]

618.0 mg; white powder.

(i) Surface Tension-Reducing Effect

Highest surface tension: 21.0 dynes/cm.
Lowest surface tension: 1.7 dynes/cm.

(ii) Spreadability Over a Gas-Liquid Interface

Equilibration time: 90 seconds.
Equilibrium surface tension: 28.3 dynes/cm.

(iii) Alveolar Volume-Maintaining Effect

Alveolar volume (at 5 cmH$_2$O): 42 ml/kg.

EXAMPLE 17

[Chemical Composition]

| Component | Content |
| --- | --- |
| 1,2-Dipalmitoylglycero-(3)-phosphocholine | 66.6% (w/w) |
| 1,2-Diacyl-sn-glycero-(3)-phospho-sn-glycerol | 20.5% (w/w) |
| Palmitic acid | 5.9% (w/w) |
| Stearic acid | 2.0% (w/w)  (total) 8.9% (w/w) |
| Oleic acid | 1.0% (w/w) |
| Lipoprotein | 2.0% (w/w) |
| Water | 2.0% (w/w) |

[Yield and Appearance]

612.0 mg; yellowish-white powder.

(i) Surface Tension-Reducing Effect

Highest surface tension: 27.8 dynes/cm.
Lowest surface tension: 1.8 dynes/cm.

(ii) Spreadability Over a Gas-Liquid Interface

Equilibration time: 40 seconds.
Equilibrium surface tension: 29.1 dynes/cm.

(iii) Alveolar Volume-Maintaining Effect

Alveolar volume (at 5 cmH$_2$O): 51 ml/kg.

EXAMPLE 18

After being sterilized, 330.0 mg of 1,2-distearoylglycero-(3)-phosphocholine, 110.0 mg of 1,2-diacyl-sn-glycero-(3)-phospho-sn-glycerol (with acyl groups having 14 to 24 carbon atoms; Sigma Chemicals Co.), 45.5 mg of palmitic acid and 15.5 mg of the lipoprotein prepared in Reference Example 2 were added to and dissolved in 500 ml of a chloroform-methanol mixture (with a volume ratio of 2.5:1). The solvent of this solution was distilled off and the resulting residue was suspended in 180 ml of a water-ethanol mixture (with a volume ratio of 10:1) at 40° C. over a period of 25 minutes. This suspension was frozen at −45° C. and dried at a vacuum of 70–90 μmHg for 36 hours to obtain a surfactant.

[Chemical Composition]

| Component | Content |
| --- | --- |
| 1,2-Distearoylglycerol-(3)-phosphocholine | 64.6% (w/w) |
| 1,2-Diacyl-sn-glycerol-(3)-phospho-sn-glycerol | 21.5% (w/w) |
| Palmitic acid | 8.7% (w/w) |
| Lipoprotein | 3.0% (w/w) |
| Water | 2.2% (w/w) |

[Yield and Appearance]

511.0 mg; white powder.

(i) Surface Tension-Reducing Effect

Highest surface tension: 34.7 dynes/cm.
Lowest surface tension: 7.2 dynes/cm.

(ii) Spreadability Over a Gas-Liquid Interface

Equilibration time: 90 seconds.
Equilibrium Surface Tension: 29.0 dynes/cm.

(iii) Alveolar Volume-Maintaining Effect

Alveolar volume (at 5 cmH$_2$O): 37 ml/kg.

In addition, three other surfactants in Examples 19–21 below were prepared in all the same manner as described above, except that 330.0 mg of 1-stearoyl-2-palmitoylglycero-(3)-phosphocholine, 1-hexadecyl-2-palmitoylglycero-(3)-phosphocholine or 1,2-dihexadecylglycero-(3)-phosphocholine was used in place of the 1,2-distearoylglycero-(3)-phosphocholine (330.0 mg).

EXAMPLE 19

[Chemical Composition]

| Component | Content |
| --- | --- |
| 1-Stearoyl-2-palmitoylglycero-(3)-phosphocholine | 63.0% (w/w) |
| 1,2-Diacyl-sn-glycero-(3)-phospho-sn-glycerol | 21.0% (w/w) |
| Palmitic acid | 8.5% (w/w) |
| Lipoprotein | 3.0% (w/w) |
| Water | 4.5% (w/w) |

[Yield and Appearance]

523.5 mg; white powder.

(i) Surface Tension-Reducing Effect

Highest surface tension: 30.8 dynes/cm.
Lowest surface tension: 5.3 dynes/cm.

(ii) Spreadability Over a Gas-Liquid Interface

Equilibration time: 75 seconds.
Equilibrium surface tension: 31.1 dynes/cm.

(iii) Alveolar Volume-Maintaining Effect

Alveolar volume (at 5 cmH$_2$O): 44 ml/kg.

EXAMPLE 20

[Chemical Composition]

| Component | Content |
| --- | --- |
| 1-Hexadecyl-2-palmitoylglycero-(3)-phosphochline | 63.8% (w/w) |
| 1,2-Diacyl-sn-glycero-(3)-phospho-sn-glycerol | 21.3% (w/w) |
| Palmitic acid | 8.6% (w/w) |
| Lipoprotein | 3.0% (w/w) |
| Water | 3.3% (w/w) |

[Yield and Appearance]

517.0 mg; white powder.

(i) Surface Tension-Reducing Effect

Highest surface tension: 26.6 dynes/cm.

Lowest surface tension: 1.2 dynes/cm.

(ii) Spreadability Over a Gas-Liquid Interface

Equilibration time: 35 seconds.
Equilibrium surface tension: 26.9 dynes/cm.

(iii) Alveolar Volume-Maintaining Effect

Alveolar volume (at 5 cmH$_2$O): 51 ml/kg.

EXAMPLE 21

[Chemical Composition]

| Component | Content |
| --- | --- |
| 1,2-Dihexadecylglycero-(3)-phosphocholine | 63.5% (w/w) |
| 1,2-Diacyl-sn-glycero-(3)-phospho-sn-glycerol | 21.2% (w/w) |
| Palmitic acid | 8.6% (w/w) |
| Lipoprotein | 3.0% (w/w) |
| Water | 3.7% (w/w) |

[Yield And Appearance]

520.0 mg; white powder.

(i) Surface Tension-Reducing Effect

Highest surface tension: 26.3 dynes/cm.
Lowest surface tension: 1.0 dynes/cm.

(ii) Spreadability Over a Gas-Liquid Interface

Equilibration time: 30 seconds.
Equilibrium surface tension: 26.7 dynes/cm.

(iii) Alveolar Volume-Maintaining Effect

Alveolar volume (at 5 cmH$_2$O): 51 mg/kg.

EXAMPLE 22

After being sterilized, 330.0 mg of 1,2-distearoylglycero-(3)-phosphocholine, 110.0 mg of 1,2-diacyl-sn-glycero-(3)-phospho-L-serine (with acyl groups having 14 to 24 carbon atoms; Sigma Chemicals Co.), 44.5 mg of palmitic acid and 15.5 mg of the lipoprotein prepared in Reference Example 1 were added to and dissolved in 500 ml of a chloroform-methanol mixture (with a volume ratio of 2.5:1). This solution was evaporated to dryness under reduced pressure and the resulting residue was suspended in 180 ml of a water-ethanol mixture (with a volume ratio of 10:1) at 40° C. over a period of 25 minutes. This suspension was frozen at −45° C. and dried at a vacuum of 70–90 μmHg for 36 hours to obtain a surfactant.

[Chemical Composition]

| Component | Content |
| --- | --- |
| 1,2-Distearoylglycero-(3)-phosphocholine | 64.4% (w/w) |
| 1,2-Diacyl-sn-glycero-(3)-phospho-L-serine | 21.4% (w/w) |
| Palmitic acid | 8.7% (w/w) |
| Lipoprotein | 3.0% (w/w) |
| Water | 2.5% (w/w) |

[Yield and Appearance]

512.5 mg; white powder.

(i) Surface Tension-Reducing Effect

Highest surface tension: 34.3 dynes/cm.
Lowest surface tension: 9.2 dynes/cm.

(ii) Spreadability Over a Gas-Liquid Interface

Equilibration time: 100 seconds.
Equilibrium surface tension: 32.3 dynes/cm.

(iii) Alveolar Volume-Maintaining Effect

Alveolar volume (at 5 cmH$_2$O): 35 ml/kg.

In addition, three other surfactants in Examples 23–25 below were prepared in all the same manner as described above, except that 330.0 mg of 1-palmitoyl-2-stearoylglycero-(3)-phosphocholine, 1-hexadecyl-2-palmitoylglycero-(3)-phosphocholine or 1,2-dihexadecylglycero-(3)-phosphocholine was used in place of the 1,2-distearoylglycero-(3)-phosphocholine (330.0 mg).

EXAMPLE 23

[Chemical Composition]

| Component | Content |
| --- | --- |
| 1-Palmitoyl-2-stearoylglycero-(3)-phosphocholine | 64.6% (w/w) |
| 1,2-Diacyl-sn-glycero-(3)-phospho-L-serine | 21.5% (w/w) |
| Palmitic acid | 8.7% (w/w) |
| Lipoprotein | 3.0% (w/w) |
| Water | 2.2% (w/w) |

[Yield and Appearance]

511.0 mg; white powder.

(i) Surface Tension-Reducing Effect

Highest surface tension: 32.3 dynes/cm.
Lowest surface tension: 6.6 dynes/cm.

(ii) Spreadability Over a Gas-Liquid Interface

Equilibration time: 70 seconds.
Equilibrium surface tension: 33.2 dynes/cm.

(iii) Alveolar Volume-Maintaining Effect

Alveolar volume (at 5 cmH$_2$O): 46 ml/kg.

EXAMPLE 24

[Chemical Composition]

| Component | Content |
| --- | --- |
| 1-Hexadecyl-2-palmitoylglycero-(3)-phosphocholine | 64.1% (w/w) |
| 1,2-Diacyl-sn-glycero-(3)-phospho-L-serine | 21.4% (w/w) |
| Palmitic acid | 8.6% (w/w) |
| Lipoprotein | 3.0% (w/w) |
| Water | 2.9% (w/w) |

[Yield and Appearance]

515.0 mg; white powder.

(i) Surface Tension-Reducing Effect

Highest surface tension: 24.6 dynes/cm.
Lowest surface tension: 0.8 dynes/cm.

(ii) Spreadability Over a Gas-Liquid Interface

Equilibration time: 45 seconds.
Equilibrium surface tension: 27.9 dynes/cm.

(iii) Alveolar Volume-Maintaining Effect

Alveolar volume (at 5 cmH$_2$O): 52 ml/kg.

EXAMPLE 25

[Chemical Composition]

| Component | Content |
| --- | --- |
| 1,2-Dihexadecylglycero-(3)-phosphocholine | 63.8% (w/w) |
| 1,2-Diacyl-sn-glycero-(3)-phospho-L-serine | 21.2% (w/w) |
| Palmitic acid | 8.6% (w/w) |
| Lipoprotein | 3.0% (w/w) |
| Water | 3.4% (w/w) |

[Yield and Appearance]

517.5 mg; white powder.

(i) Surface Tension-Reducing Effect

Highest surface tension: 24.1 dynes/cm.
Lowest surface tension: 0.9 dynes/cm.

(ii) Spreadability Over a Gas-Liquid Interface

Equilibration time: 45 seconds.
Equilibrium surface tension: 28.6 dynes/cm.

(iii) Alveolar Volume-Maintaining Effect

Alveolar volume (at 5 cmH$_2$O): 51 ml/kg.

EXAMPLE 26

After being sterilized, 400.0 mg of 1,2-dipalmitoyl-glycero-(3)-phosphocholine, 44.5 mg of 1,2-diacyl-sn-glycero-(3)-phospho-sn-glycerol (with acyl groups having 14 to 24 carbon atoms; Sigma Chemicals Co.), 44.5 mg of palmitic acid and 11.0 mg of the lipoprotein prepared in Reference Example 2 were added to and dissolved in 530 ml of a chloroform-methanol mixture (with a volume ratio of 2:1). This solution was evaporated to dryness under reduced pressure and the resulting residue was suspended in 190 ml of a water-ethanol mixture (with a volume ratio of 9:1) at 40° C. over a period of 30 minutes. This suspension was frozen at −50° C. and dried at a vacuum of 60–90 μmHg for 36 hours to obtain a surfactant.

[Chemical Composition]

| Component | Content |
| --- | --- |
| 1,2-Dipalmitoylglycero-(3)-phosphocholine | 79.3% (w/w) |
| 1,2-Diacyl-sn-glycero-(3)-phospho-sn-glycerol | 8.8% (w/w) |
| Palmitic acid | 8.8% (w/w) |
| Lipoprotein | 2.2% (w/w) |
| Water | 0.9% (w/w) |

[Yield and Appearance]

504.5 mg; white powder.

(i) Surface Tension-Reducing Effect

Highest surface tension: 27.0 dynes/cm.
Lowest surface tension: 0.5 dynes/cm.

(ii) Spreadability Over a Gas-Liquid Interface

Equilibration time: 100 seconds.
Equilibrium surface tension: 34.9 dynes/cm.

(iii) Alveolar Volume-Maintaining Effect

Alveolar volume (at 5 cmH$_2$O): 36 ml/kg.

In addition, three other surfactants in Examples 27–29 below were prepared by using 1,2-dipalmitoyl-glycero-(3)-phosphocholine and 1,2-diacyl-sn-glycero-(3)-phospho-sn-glycerol in amounts of 355.5 mg and 89.0 mg, 311.0 mg and 133.5 mg, or 255.0 mg and 189.5 mg, respectively. The amounts of the two other components and the preparation procedure remained unchanged.

EXAMPLE 27

[Chemical Composition]

| Component | Content |
| --- | --- |
| 1,2-Dipalmitoylglycero-(3)-phosphocholine | 69.8% (w/w) |
| 1,2-Diacyl-sn-glycero-(3)-phospho-sn-glycerol | 17.5% (w/w) |
| Palmitic acid | 8.7% (w/w) |
| Lipoprotein | 2.2% (w/w) |
| Water | 1.8% (w/w) |

[Yield and Appearance]

509.5 mg; white powder.

(i) Surface Tension-Reducing Effect

Highest surface tension: 29.7 dynes/cm.
Lowest surface tension: 1.2 dynes/cm.

(ii) Spreadability Over a Gas-Liquid Interface

Equilibration time: 55 seconds
Equilibrium surface tension: 29.1 dynes/cm.

(iii) Alveolar Volume-Maintaining Effect

Alveolar volume (at 5 cmH$_2$O): 49 ml/kg.

EXAMPLE 28

[Chemical Composition]

| Component | Content |
| --- | --- |
| 1,2-Dipalmitoylglycero-(3)-phosphocholine | 61.5% (w/w) |
| 1,2-Diacyl-sn-glycero-(3)-phospho-sn-glycerol | 26.4% (w/w) |
| Palmitic acid | 8.8% (w/w) |
| Lipoprotein | 2.2% (w/w) |
| Water | 1.1% (w/w) |

[Yield and Appearance]

505.5 mg; yellowish-white powder.

(i) Surface Tension-Reducing Effect

Highest surface tension: 28.3 dynes/cm.
Lowest surface tension: 2.7 dynes/cm.

(ii) Spreadability Over a Gas-Liquid Interface

Equilibration time: 30 seconds.
Equilibrium surface tension: 26.9 dynes/cm.

(iii) Alveolar Volume-Maintaining Effect

Alveolar volume (at 5 cmH$_2$O): 51 ml/kg.

EXAMPLE 29

[Chemical Composition]

| Component | Content |
| --- | --- |
| 1,2-Dipalmitoylglycero-(3)-phosphocholine | 50.6% (w/w) |

-continued

| Component | Content |
|---|---|
| 1,2-Diacyl-sn-glycero-(3)-phospho-sn-glycerol | 37.6% (w/w) |
| Palmitic acid | 8.8% (w/w) |
| Lipoprotein | 2.2% (w/w) |
| Water | 0.8% (w/w) |

[Yield and Appearance]

504.0 mg; pale-yellow powder.

(i) Surface Tension-Reducing Effect

Highest surface tension: 30.4 dynes/cm.
Lowest surface tension: 4.6 dynes/cm.

(ii) Spreadability Over a Gas-Liquid Interface

Equilibration time: 75 seconds.
Equilibrium surface tension: 29.3 dynes/cm.

(iii) Alveolar Volume-Maintaining Effect

Alveolar volume (at 5 cmH$_2$O): 40 ml/kg.

EXAMPLE 30

After being sterilized, 370.0 mg of 1,2-dipalmitoyl-glycero-(3)-phosphocholine, 130.0 mg of 1,2-diacyl-sn-glycero-(3)-phospho-sn-glycerol (with acyl groups having 14 to 24 carbon atoms; Sigma Chemicals Co.), 25.0 mg of palmitic acid and 10.0 mg of the lipoprotein prepared in Reference Example 1 were added to and dissolved in 630 ml of a chloroform-methanol mixture (with a volume ratio of 2:1). This solution was evaporated to dryness under reduced pressure and the resulting residue was suspended in 200 ml of a water-ethanol mixture (with a volume ratio of 8:1) at 45° C. over a period of 25 minutes. This suspension was frozen at −50° C. and dried at a vacuum of 80–100 μmHg for 30 hours to obtain a surfactant.

[Chemical Composition]

| Component | Content |
|---|---|
| 1,2-Dipalmitoylglycero-(3)-phosphocholine | 67.8% (w/w) |
| 1,2-Diacyl-sn-glycero-(3)-phospho-sn-glycerol | 23.8% (w/w) |
| Palmitic acid | 4.6% (w/w) |
| Lipoprotein | 1.8% (w/w) |
| Water | 2.0% (w/w) |

[Yield and Appearance]

546.0 mg; white powder.

(i) Surface Tension-Reducing Effect

Highest surface tension: 28.0 dynes/cm.
Lowest surface tension: 2.7 dynes/cm.

(ii) Spreadability Over a Gas-Liquid Interface

Equilibration time: 90 seconds.
Equilibrium surface tension: 23.9 dynes/cm.

(iii) Alveolar Volume-Maintaining Effect

Alveolar volume (at 5 cmH$_2$O): 44 ml/kg.

In Examples 31–33, three other surfactants were prepared in all the same manner as described above, except that the amount of palmitic acid used was increased to 90.0 mg, 129.0 mg or 168.1 mg. In Examples 34–37, four other surfactants were prepared by replacing the palmitic acid and the 1,2-diacyl-sn-glycero-(3)-phospho-sn-glycerol with stearic acid and 1,2-diacyl-sn-glycerol-(3)-phospho-L-serine (with acyl groups having 14 to 24 carbon atoms; Sigma Chemicals Co.) and using them in amounts of 25.0 mg and 130.0 mg, 35.0 mg and 130.0 mg, 50.0 mg and 130.0 mg, or 65.0 mg and 130.0 mg, respectively. The amounts of the two other components (i.e., 1,2-dipalmitoylglycero-(3)-phosphocholine and lipoprotein) and the preparation procedure remained unchanged.

EXAMPLE 31

[Chemical Composition]

| Component | Content |
|---|---|
| 1,2-Dipalmitoylglycero-(3)-phosphocholine | 60.3% (w/w) |
| 1,2-Diacyl-sn-glycero-(3)-phospho-sn-glycerol | 21.2% (w/w) |
| Palmitic acid | 14.6% (w/w) |
| Lipoprotein | 1.6% (w/w) |
| Water | 2.3% (w/w) |

[Yield and Appearance]

613.0 mg; white powder.

(i) Surface Tension-Reducing Effect

Highest surface tension: 26.8 dynes/cm.
Lowest surface tension: 3.3 dynes/cm.

(ii) Spreadability Over a Gas-Liquid Interface

Equilibration time: 35 seconds.
Equilibrium surface tension: 30.2 dynes/cm.

(iii) Alveolar Volume-Maintaining Effect

Alveolar volume (at 5 cmH$_2$O): 51 ml/kg.

EXAMPLE 32

[Chemical Composition]

| Component | Content |
|---|---|
| 1,2-Dipalmitoylglycero-(3)-phosphocholine | 57.3% (w/w) |
| 1,2-Diacyl-sn-glycero-(3)-phospho-sn-glycerol | 20.1% (w/w) |
| Palmitic acid | 20.0% (w/w) |
| Lipoprotein | 1.5% (w/w) |
| Water | 1.1% (w/w) |

[Yield and Appearance]

646.0 mg; white powder.

(i) Surface Tension-Reducing Effect

Highest surface tension: 26.9 dynes/cm.
Lowest surface tension: 6.7 dynes/cm.

(ii) Spreadability Over a Gas-Liquid Interface

Equilibration time: 85 seconds.
Equilibrium surface tension: 31.1 dynes/cm.

(iii) Alveolar Volume-Maintaining Effect

Alveolar volume (at 5 cmH$_2$O): 42 ml/kg.

EXAMPLE 33

[Chemical Composition]

| Component | Content |
|---|---|
| 1,2-Dipalmitoylglycero-(3)-phosphocholine | 54.1% (w/w) |
| 1,2-Diacyl-sn-glycero-(3)-phospho-sn-glycerol | 19.0% (w/w) |
| Palmitic acid | 24.6% (w/w) |
| Lipoprotein | 1.5% (w/w) |
| Water | 0.8% (w/w) |

[Yield and Appearance]

683.4 mg; white powder.

(i) Surface Tension-Reducing Effect

Highest surface tension: 34.8 dynes/cm.
Lowest surface tension: 10.0 dynes/cm.

(ii) Spreadability Over a Gas-Liquid Interface

Equilibration time: 95 seconds.
Equilibrium surface tension: 34.4 dynes/cm.

(iii) Alveolar Volume-Maintaining Effect

Alveolar volume (at 5 cmH$_2$O): 35 ml/kg.

EXAMPLE 34

[Chemical Composition]

| Component | Content |
|---|---|
| 1,2-Dipalmitoylglycero-(3)-phosphocholine | 67.5% (w/w) |
| 1,2-Diacyl-sn-glycero-(3)-phospho-L-serine | 23.7% (w/w) |
| Stearic acid | 4.6% (w/w) |
| Lipoprotein | 1.8% (w/w) |
| Water | 2.4% (w/w) |

[Yield and Appearance]

548.0 mg; yellowish-white powder.

(i) Surface Tension-Reducing Effect

Highest surface tension: 18.5 dynes/cm.
Lowest surface tension: 0.4 dynes/cm.

(ii) Spreadability Over a Gas-Liquid Interface

Equilibration time: 50 seconds.
Equilibrium surface tension: 28.5 dynes/cm.

(iii) Alveolar Volume-Maintaining Effect

Alveolar volume (at 5 cmH$_2$O): 43 ml/kg.

EXAMPLE 35

[Chemical Composition]

| Component | Content |
|---|---|
| 1,2-Dipalmitoylglycero-(3)-phosphocholine | 66.0% (w/w) |
| 1,2-Diacyl-sn-glycero-(3)-phospho-L-serine | 23.2% (w/w) |
| Stearic acid | 6.2% (w/w) |
| Lipoprotein | 1.8% (w/w) |
| Water | 2.8% (w/w) |

[Yield and Appearance]

560.9 mg; white powder.

(i) Surface Tension-Reducing Effect

Highest surface tension: 20.8 dynes/cm.
Lowest surface tension: 0.9 dynes/cm.

(ii) Spreadability Over a Gas-Liquid Interface

Equilibration time: 45 seconds.
Equilibrium surface tension: 28.3 dynes/cm.

(iii) Alveolar Volume-Maintaining Effect

Alveolar volume (at 5 cmH$_2$O): 48 ml/kg.

EXAMPLE 36

[Chemical Composition]

| Component | Content |
|---|---|
| 1,2-Dipalmitoylglycero-(3)-phosphocholine | 64.9% (w/w) |
| 1,2-Diacyl-sn-glycero-(3)-phospho-L-serine | 22.8% (w/w) |
| Stearic acid | 8.8% (w/w) |
| Lipoprotein | 1.8% (w/w) |
| Water | 1.7% (w/w) |

[Yield and Appearance]

569.8 mg; white powder.

(i) Surface Tension-Reducing Effect

Highest surface tension: 23.8 dynes/cm.
Lowest surface tension: 1.2 dynes/cm.

(ii) Spreadability Over a Gas-Liquid Interface

Equilibration time: 35 seconds.
Equilibrium surface tension: 27.1 dynes/cm.

(iii) Alveolar Volume-Maintaining Effect

Alveolar volume (at 5 cmH$_2$O): 51 ml/kg.

EXAMPLE 37

[Chemical Composition]

| Component | Content |
|---|---|
| 1,2-Dipalmitoylglycero-(3)-phosphocholine | 62.8% (w/w) |
| 1,2-Diacyl-sn-glycero-(3)-phospho-L-serine | 22.1% (w/w) |
| Stearic acid | 11.0% (w/w) |
| Lipoprotein | 1.7% (w/w) |
| Water | 2.4% (w/w) |

[Yield and Appearance]

589.0 mg; white powder.

(i) Surface Tension-Reducing Effect

Highest surface tension: 25.1 dynes/cm.
Lowest surface tension: 3.4 dynes/cm.

(ii) Spreadability Over a Gas-Liquid Interface

Equilibration time: 50 seconds.
Equilibrium surface tension: 30.8 dynes/cm.

(iii) Alveolar Volume-Maintaining Effect

Alveolar volume (at 5 cmH$_2$O): 40 ml/kg.

EXAMPLE 38

After being sterilized, 760.0 mg of 1,2-dipalmitoyl-glycero-(3)-phosphocholine, 240.0 mg of 1,2-diacyl-snglycero-(3)-phospho-sn-glycerol (with acyl groups having 16 to 18 carbon atoms), 100.0 mg of palmitic acid and 1.0 mg of the lipoprotein prepared in Reference Example 1 were added to and dissolved in 1,000 ml of a chloroform-methanol mixture (with a volume ratio of 2:1). The solvent of this solution was distilled off under reduced pressure and the resulting residue was suspended in 380 ml of a water-ethanol mixture (with a volume ratio of 9:1) at 40° C. over a period of 30 minutes. This suspension was frozen at −40° C. and dried at a vacuum of 80–90 μmHg for 36 hours to obtain a surfactant.

[Chemical Composition]

| Component | Content |
| --- | --- |
| 1,2-Dipalmitoylglycero-(3)-phosphocholine | 67.8% (w/w) |
| 1,2-Diacyl-sn-glycero-(3)-phospho-sn-glycerol | 21.4% (w/w) |
| Palmitic acid | 8.9% (w/w) |
| Lipoprotein | 0.1% (w/w) |
| Water | 1.8% (w/w) |

[Yield and Appearance]

1,121.0 mg; white powder.

(i) Surface Tension-Reducing Effect

Highest surface tension: 23.2 dynes/cm.
Lowest surface tension: 2.0 dynes/cm.

(ii) Spreadability Over a Gas-Liquid Interface

Equilibration time: 80 seconds.
Equilibrium surface tension: 32.4 dynes/cm.

(iii) Alveolar Volume-Maintaining Effect

Alveolar volume (at 5 cmH$_2$O): 37 ml/kg.

In Examples 39–41, three other surfactants were prepared in all the same manner as described above, except that the amount of lipoprotein used was increased to 5.0 mg, 59.0 mg or 123.7 mg.

EXAMPLE 39

[Chemical Composition]

| Component | Content |
| --- | --- |
| 1,2-Dipalmitoylglycero-(3)-phosphocholine | 66.3% (w/w) |
| 1,2-Diacyl-sn-glycero-(3)-phospho-sn-glycerol | 20.9% (w/w) |
| Palmitic aicd | 8.7% (w/w) |
| Lipoprotein | 0.4% (w/w) |
| Water | 3.7% (w/w) |

[Yield and Appearance]

1,147.0 mg; white powder.

(i) Surface Tension-Reducing Effect

Highest surface tension: 26.0 dynes/cm.
Lowest surface tension: 1.2 dynes/cm.

(ii) Spreadability Over a Gas-Liquid Interface

Equilibration time: 65 seconds.
Equilibrium surface tension: 27.6 dynes/cm.

(iii) Alveolar Volume-Maintaining Effect

Alveolar volume (at 5 cmH$_2$O): 49 ml/kg.

EXAMPLE 40

[Chemical Composition]

| Component | Content |
| --- | --- |
| 1,2-Dipalmitoylglycero-(3)-phosphocholine | 64.0% (w/w) |
| 1,2-Diacyl-sn-glycero-(3)-phospho-sn-glycerol | 20.2% (w/w) |
| Palmitic acid | 8.4% (w/w) |
| Lipoprotein | 5.0% (w/w) |
| Water | 2.4% (w/w) |

[Yield and Appearance]

1,187.0 mg; white powder.

(i) Surface Tension-Reducing Effect

Highest surface tension: 28.1 dynes/cm.
Lowest surface tension: 2.7 dynes/cm.

(ii) Spreadability Over a Gas-Liquid Interface

Equilibration time: 65 seconds.
Equilibrium surface tension: 28.8 dynes/cm.

(iii) Alveolar Volume-Maintaining Effect

Alveolar volume (at 5 cmH$_2$O): 46 ml/kg.

EXAMPLE 41

[Chemical Composition]

| Component | Content |
| --- | --- |
| 1,2-Dipalmitoylglycero-(3)-phosphocholine | 61.4% (w/w) |
| 1,2-Diacyl-sn-glycero-(3)-phospho-sn-glycerol | 19.4% (w/w) |
| Palmitic acid | 8.1% (w/w) |
| Lipoprotein | 10.0% (w/w) |
| Water | 1.1% (w/w) |

[Yield and Appearance]

1,237.4 mg; yellowish-white powder.

(i) Surface Tension-Reducing Effect

Highest surface tension: 28.8 dynes/cm.
Lowest surface tension: 3.1 dynes/cm.

(ii) Spreadability Over a Gas-Liquid Interface

Equilibration time: 70 seconds.
Equilibrium surface tension: 29.8 dynes/cm.

(iii) Alveolar Volume-Maintaining Effect

Alveolar volume (at 5 cmH$_2$O): 43 ml/kg.

EXAMPLE 42

After being sterilized, 300.0 mg of 1,2-dihexadecyl-glycero-(3)-phosphocholine, 100.0 mg of 1,2-diacyl-sn-glycero-(3)-phosphate (with acyl groups having 14 to 24 carbon atoms; Serdary Research Laboratories Inc.), 40.0 mg of palmitic acid and 9.0 mg of the lipoprotein prepared in Reference Example 1 were added to and dissolved in 480 ml of a chloroform-methanol mixture (with a volume ratio of 2:1). This solution was evaporated to dryness under reduced pressure and the resulting residue was suspended in a water-ethanol mixture (with a volume ratio of 20:1) at 40° C. over a period of 30 minutes. This suspension was frozen at −50° C. and dried at a vacuum of 50–100 μmHg for 30 hours to obtain a yield of 460.2 mg of surfactant in the form of a pale-yellow powder. No residual ethanol was detected in this powder.

[Chemical Composition]

| Component | Content |
| --- | --- |
| 1,2-Dihexadecylglycero-(3)-phosphocholine | 65.2% (w/w) |
| 1,2-Diacyl-sn-glycero-(3)-phosphate | 21.7% (w/w) |
| Palmitic acid | 8.7% (w/w) |
| Lipoprotein | 2.0% (w/w) |
| Water | 2.4% (w/w) |

(i) Surface Tension-Reducing Effect

Highest surface tension: 29.2 dynes/cm.
Lowest surface tension: 5.3 dynes/cm.

(ii) Spreadability Over a Gas-Liquid Interface

Equilibration time: 80 seconds.
Equilibrium surface tension: 30.4 dynes/cm.

(iii) Alveolar Volume-Maintaining Effect

Alveolar volume (at 5 cmH$_2$O): 41 ml/kg.

EXAMPLE 43

The procedure of Example 42 was repeated except that 40.0 mg of hexadecyl alcohol was used in place of the palmitic acid (40.0 mg). Thus, there was obtained a yield of 457.3 mg of surfactant in the form of a pale-yellow powder. Its test for ethanol gave negative results.

[Chemical Composition]

| Component | Content |
| --- | --- |
| 1,2-Dihexadecylglycero-(3)-phosphocholine | 65.6% (w/w) |
| 1,2-Diacyl-sn-glycero-(3)-phosphate | 21.9% (w/w) |
| Hexadecyl alcohol | 8.7% (w/w) |
| Lipoprotein | 2.0% (w/w) |
| Water | 1.8% (w/w) |

(i) Surface Tension-Reducing Effect

Highest surface tension: 34.9 dynes/cm.
Lowest surface tension: 8.7 dynes/cm.

(ii) Spreadability Over a Gas-Liquid Interface

Equilibration time: 95 seconds.
Equilibrium surface tension: 34.7 dynes/cm.

(iii) Alveolar Volume-Maintaining Effect

Alveolar volume (at 5 cmH$_2$O): 37 ml/kg.

EXAMPLE 44

After being sterilized, 300.0 mg of 1,2-dipalmitoyl-glycero-(3)-phosphocholine (L-isomer), 100.0 mg of 1,2-diacyl-sn-glycero-(3)-phospho-sn-glycerol (with acyl groups having 14 to 24 carbon atoms; Sigma Chemicals Co.), 40.0 mg of palmitic acid and 8.0 mg of the lipoprotein prepared in Reference Example 1 were added to and dissolved in 450 ml of a chloroformmethanol mixture (with a volume ratio of 2:1). This solution was evaporated to dryness under reduced pressure and the resulting residue was suspended in 150 ml of a water-ethanol mixture (with a volume ratio of 4:1) at 40° C. over a period of 30 minutes. This suspension was frozen at −80° C. and dried at a vacuum of 50–70 μmHg for 24 hours to obtain a yield of 459.7 mg of surfactant in the form of a white powder. No residual ethanol was detected in this powder.

[Chemical Composition]

| Component | Content |
| --- | --- |
| 1,2-Dipalmitoylglycero-(3)-phosphocholine (L-isomer) | 65.3% (w/w) |
| 1,2-Diacyl-sn-glycero-(3)-phospho-sn-glycerol | 21.8% (w/w) |
| Palmitic acid | 8.7% (w/w) |
| Lipoprotein | 1.7% (w/w) |
| Water | 2.5% (w/w) |

(i) Surface Tension-Reducing Effect

Highest surface tension: 26.5 dynes/cm.
Lowest surface tension: 2.3 dynes/cm.

(ii) Spreadability Over a Gas-Liquid Interface

Equilibration time: 40 seconds.
Equilibrium surface tension: 28.7 dynes/cm.

(iii) Alveolar Volume-Maintaining Effect

Alveolar volume (at 5 cmH$_2$O): 52 ml/kg.

EXAMPLE 45

The procedure of Example 44 was repeated except that 300.0 mg of 1,2-dipalmitoylglycero-(3)-phosphocholine (D-isomer) was used in place of the 1,2-dipalmitoylglycero-(3)-phosphocholine (L-isomer) (300.0 mg). Thus, there was obtained a yield of 462.6 mg of surfactant in the form of a white powder. No residual ethanol was detected in this powder.

[Chemical Composition]

| Component | Content |
| --- | --- |
| 1,2-Dipalmitoylglycero-(3)-phosphocholine (D-isomer) | 64.9% (w/w) |
| 1,2-Diacyl-sn-glycero-(3)-phospho-sn-glycerol | 21.6% (w/w) |
| Palmitic acid | 8.6% (w/w) |
| Lipoprotein | 1.7% (w/w) |
| Water | 3.2% (w/w) |

(i) Surface Tension-Reducing Effect

Highest surface tension: 27.0 dynes/cm.
Lowest surface tension: 1.9 dynes/cm.

(ii) Spreadability Over a Gas-Liquid Interface

Equilibration time: 35 seconds.
Equilibrium surface tension: 27.3 dynes/cm.

(iii) Alveolar Volume-Maintaining Effect

Alveolar volume (at 5 cmH$_2$O): 53 ml/kg.

EXAMPLE 46

After being sterilized, 400.0 mg of 1,2-dipalmitoyl-glycero-(3)-phosphocholine, 167.0 mg of 1,2-diacyl-sn-glycero-(3)-phosphocholine (with acyl groups having 14 to 24 carbon atoms; Sigma Chemicals Co.), 30.0 mg of 1,2-diacyl-sn-glycero-(3)-phospho-sn-glycerol (with acyl groups having 14 to 24 carbon atoms; Sigma Chemicals Co.), 54.0 mg of palmitic acid and 10.0 mg of the lipoprotein prepared in Reference Example 1 were added to and dissolved in 450 ml of a chloroformmethanol mixture (with a volume ratio of 2:1). This solution was treated in all the same manner as in Example 44 to obtain a yield of 667.0 mg of surfactant in the form of a yellowish-white powder.

[Chemical Composition]

| Component | Content | |
|---|---|---|
| 1,2-Dipalmitoylglycero-(3)-phosphocholine | 60.0% (w/w) | (total) 85.0% (w/w) |
| 1,2-Diacyl-sn-glycero-(3)-phosphocholine | 25.0% (w/w) | |
| 1,2-Diacyl-sn-glycero-(3)-phospho-sn-glycerol | 4.5% (w/w) | |
| Palmitic acid | 8.1% (w/w) | |
| Lipoprotein | 1.5% (w/w) | |
| Water | 0.9% (w/w) | |

(i) Surface Tension-Reducing Effect

Highest surface tension: 33.7 dynes/cm.
Lowest surface tension: 8.9 dynes/cm.

(ii) Spreadability Over a Gas-Liquid Interface

Equilibration time: 85 seconds.
Equilibrium surface tension: 34.8 dynes/cm.

(iii) Alveolar Volume-Maintaining Effect

Alveolar volume (at 5 cmH$_2$O): 36 ml/kg.

EXAMPLE 47

After being sterilized, 533.6 mg of 1,2-dipalmitoyl-glycero-(3)-phosphocholine, 177.6 mg of 1,2-diacyl-sn-glycero-(3)-phospho-sn-glycerol (with acyl groups having 14 to 24 carbon atoms; Sigma Chemicals Co.), 71.2 mg of palmitic acid and 17.6 mg of the lipoprotein prepared in Reference Example 1 were placed in an agate mortar. These components were kneaded together for 30 minutes, during which time 5 ml of a chloroformmethanol mixture (with a volume ratio of 2:1) was added dropwise in several steps. The resulting slurry was vacuum-dried at 5° C. for 24 hours to obtain a yield of 770.3 mg of surfactant in the form of a pale-yellow powder.

[Chemical Composition]

| Component | Content |
|---|---|
| 1,2-Dipalmitoylglycero-(3)-phosphocholine | 66.7% (w/w) |
| 1,2-Diacyl-sn-glycero-(3)-phospho-sn-glycerol | 22.2% (w/w) |
| Palmitic acid | 8.9% (w/w) |
| Lipoprotein | 2.2% (w/w) |
| Water | 0.0% (w/w) |

(i) Surface Tension-Reducing Effect

Highest surface tension: 27.5 dynes/cm.
Lowest surface tension: 2.5 dynes/cm.

(ii) Spreadability Over a Gas-Liquid Interface

Equilibration time: 45 seconds.
Equilibrium surface tension: 27.2 dynes/cm.

(iii) Alveolar Volume-Maintaining Effect

Alveolar volume (at 5 cmH$_2$O): 50 ml/kg.
What is claimed is:

1. A surfactant consisting essentially of (1) a choline phosphoglyceride, (2) an acid phospholipid, (3) a fatty acid or its analogue, and (4) a lipoprotein derived from cattle or pig lungs, the lipoprotein being composed of 47.9 to 70.2%(w/w) of phospholipid part, 23.4 to 48.0%(w/w) of protein part, 1.8 to 5.0%(w/w) of water and 1.4 to 2.4%(w/w) of unknown component parts and having a molecular weight of 30,000 to 38,000, characterized in that the content of the choline phosphoglyceride (1) is 50.6 to 85.0%(w/w), the content of the acid phospholipid (2) is 4.5 to 37.6%(w/w), the content of the fatty acid or its analogue (3) is 4.6 to 24.6%(w/w), the content of the lipoprotein (4) is 0.1 to 10.0%(w/w), all based on the total weight of the surfactant, and characterized in that, when the surfactant is added dropwise to the surface of physiological saline at 37° C. in an amount of 0.8 to 1.5 μg per square centimeter of the surface area, the surfactant gives an equilibrium surface tension of 23.9 to 35.0 dynes/cm in a time of 30 to 100 seconds.

2. A surfactant as claimed in claim 1 wherein the lipoprotein has a specific rotatory power $[\alpha]_D^{23}$ of $-40°$ to $-85°$ at a concentration of 0.1%(w/v) in sodium dodecyl sulfate.

3. A surfactant as claimed in claim 1 wherein the choline phosphoglyceride is a member selected from the group consisting of a 1,2-diacylglycero-(3)-phosphocholine, a 1-alkyl-2-acylglycero-(3)-phosphocholine, a 1,2-dialkylglycero-(3)-phosphocholine, mixtures of two or more 1,2-diacylglycero-(3)-phosphocholines with two acyl groups having 14 to 24 carbon atoms and mixtures thereof.

4. A surfactant as claimed in claim 3 wherein the 1,2-diacylglycero-(3)-phosphocholine is a member selected from the group consisting of 1,2-dipalmitoylglycero-(3)-phosphocholine, 1,2-distearoylglycero-(3)-phosphocholine, 1-palmitoyl-2-stearoylglycero-(3)-phosphocholine, 1-stearoyl-2-palmitoylglycero-(3)-phosphocholine and mixtures thereof.

5. A surfactant as claimed in claim 3 wherein the 1-alkyl-2-acylglycero-(3)-phosphocholine is a member selected from the group consisting of 1-hexadecyl-2-palmitoylglycero-(3)-phosphocholine and 1-octadecyl-2-palmitoylglycero-(3)-phosphocholine.

6. A surfactant as claimed in claim 3 wherein the 1,2-dialkylglycero-(3)-phosphocholine is 1,2-dihexadecylglycero-(3)-phosphocholine.

7. A surfactant as claimed in claim 3,4,5 or 6 wherein the optical isomer due to the asymmetric carbon atom at the 2-position of the glycerol residue of the choline phosphoglyceride is a member selected from the group consisting of D-isomer, L-isomer and mixture thereof, when the said choline phosphoglyceride is a simple compound.

8. A surfactant as claimed in claim 1 wherein the acid phospholipid is a member selected from the group consisting of 1,2-diacyl-sn-glycero-(3)-phosphate, 1,2-diacyl-sn-glycero-(3)-phospho-L-serine, 1,2-diacyl-sn-glycero-(3)-phospho-sn-glycerol and 1,2-diacyl-sn-glycero-(3)-phospho-(1)-L-myoinositol.

9. A surfactant as claimed in claim 8 wherein the acyl groups are the same or different acyl groups having 14 to 24 carbon atoms.

10. A surfactant as claimed in claim 1 wherein the fatty acid or its analogue is a member selected from the group consisting of a free fatty acid, an alkali metal salt of a fatty acid, an alkyl ester of a fatty acid, a glyceride of a fatty acid, a fatty acid amide, a fatty alcohol, an aliphatic amine and mixtures thereof.

11. A surfactant as claimed in claim 10 wherein the free fatty acid is a member selected from the group consisting of palmitic acid, stearic acid and oleic acid.

12. A surfactant as claimed in claim 10 wherein the alkali metal salt of fatty acid is a member selected from the group consisting of sodium palmitate and sodium stearate.

13. A surfactant as claimed in claim 10 wherein the alkyl ester of fatty acid is ethyl palmitate.

14. A surfactant as claimed in claim 10 wherein the glyceride of fatty acid is a member selected from the group consisting of monopalmitin and monostearin.

15. A surfactant as claimed in claim 10 wherein the fatty acid amide is palmitic acid amide.

16. A surfactant as claimed in claim 10 wherein the fatty alcohol is a member selected from the group consisting of hexadecyl alcohol and octadecyl alcohol.

17. A surfactant as claimed in claim 10 wherein the aliphatic amine is hexadecylamine.

18. A surfactant as claimed in claim 1 wherein the content of phospholipid part is estimated by multiplying its phosphorus content by 25; the content of protein part is expressed in terms of bovine serum albumin; and the content of the unknown component parts is determined by substracting the sum of the phospholipid part, protein part and water contents from the total weight of the lipoprotein.

19. A surfactant as claimed in claim 1 wherein the molecular weight is measured according to a method based on SDS-gel electrophoresis.

20. A pharmaceutical composition useable for the treatment of respiratory distress syndrome in adult patients comprising an effective amount of from 400 to 4000 mg of a surfactant as set forth in claim 1 as a unit dosage and a pharmaceutically acceptable carrier.

21. A pharmaceutical composition useable for the treatment of respiratory distress syndrome in premature infants comprising an effective amount of from 40 to 500 mg of a surfactant as set forth in claim 1 as a unit dosage and a pharmaceutically acceptable carrier.

22. A pharmaceutical composition as claimed in claim 20 or 21 wherein the carrier is selected from the group consisting of water and physiological saline.

23. A pharmaceutical composition as claimed in claim 22 wherein the dosage form of the composition is a suspension form.

24. A method for treating respiratory distress syndrome in adult patients or premature infants comprising instilling or spraying a pharmaceutical composition as set forth in claim 20 or 21 into the airway of the corresponding patient or infant.

25. A method as claimed in claim 24 wherein, for an adult patient, the treatment is carried out one to ten times within 120 hours before or after the onset of respiratory disturbance.

26. A method as claimed in claim 24 wherein, for a premature infant, the treatment is carried out one to four times within 72 hours after birth.

* * * * *